(12) United States Patent
Blanquart et al.

(10) Patent No.: US 10,165,195 B2
(45) Date of Patent: Dec. 25, 2018

(54) WIDE DYNAMIC RANGE USING MONOCHROMATIC SENSOR

(71) Applicant: DePuy Synthes Products, Inc., Raynham, MA (US)

(72) Inventors: Laurent Blanquart, Westlake Village, CA (US); John Richardson, Westlake Village, CA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 15/483,934

(22) Filed: Apr. 10, 2017

(65) Prior Publication Data

US 2017/0214841 A1   Jul. 27, 2017

Related U.S. Application Data

(60) Continuation of application No. 15/362,512, filed on Nov. 28, 2016, now Pat. No. 9,621,817, which is a
(Continued)

(51) Int. Cl.
*H04N 5/235* (2006.01)
*A61B 1/045* (2006.01)
(Continued)

(52) U.S. Cl.
CPC ........... *H04N 5/2355* (2013.01); *A61B 1/045* (2013.01); *A61B 1/06* (2013.01); *H04N 5/2256* (2013.01); *H04N 5/2354* (2013.01); *H04N 5/35554* (2013.01); *H04N 5/37457* (2013.01); *H04N 9/045* (2013.01); *H04N 9/07* (2013.01); *H04N 13/239* (2018.05); *H04N 5/35536* (2013.01); *H04N 5/35563* (2013.01); *H04N 2209/042* (2013.01)

(58) Field of Classification Search
CPC .. H04N 5/35581; H04N 5/3728; H04N 5/347; H04N 5/35554; H04N 9/045; H04N 5/235; H04N 5/353; H04N 5/37213; H04N 5/2355; H04N 5/3595; H04N 5/2354; H04N 5/374; A61B 1/05; A61B 1/0638; A61B 1/0661
USPC ............ 348/68, 208.99, 241, 294, 317, 362
See application file for complete search history.

(56) References Cited

U.S. PATENT DOCUMENTS 4,433,675 A   2/1984   Konoshima
4,947,246 A   8/1990   Kikuchi
(Continued)

FOREIGN PATENT DOCUMENTS

EP          0912047 A2    4/1999
JP       2004-126721 A    4/2004
(Continued)

OTHER PUBLICATIONS

Computer translation of JP 2004-126721.
(Continued)

*Primary Examiner* — Nathnael Aynalem
(74) *Attorney, Agent, or Firm* — Terrence J. Edwards; TechLaw Ventures, PLLC

(57) ABSTRACT

The disclosure extends to methods, systems, and computer program products for widening dynamic range within an image in a light deficient environment.

36 Claims, 28 Drawing Sheets

Related U.S. Application Data division of application No. 13/952,564, filed on Jul. 26, 2013, now Pat. No. 9,509,917.

(60) Provisional application No. 61/790,719, filed on Mar. 15, 2013, provisional application No. 61/790,487, filed on Mar. 15, 2013, provisional application No. 61/676,289, filed on Jul. 26, 2012.

(51) Int. Cl.
| | |
|---|---|
| *A61B 1/06* | (2006.01) |
| *H04N 5/225* | (2006.01) |
| *H04N 5/355* | (2011.01) |
| *H04N 9/04* | (2006.01) |
| *H04N 9/07* | (2006.01) |
| *H04N 5/3745* | (2011.01) |
| *H04N 13/239* | (2018.01) |

(56) References Cited

U.S. PATENT DOCUMENTS

| | | |
|---|---|---|
| 5,187,572 A | 2/1993 | Nakamura et al. |
| 5,196,938 A | 3/1993 | Blessinger |
| 5,241,170 A | 8/1993 | Field, Jr. et al. |
| 5,550,595 A | 8/1996 | Hannah |
| 5,748,234 A | 5/1998 | Lippincott |
| 5,784,099 A | 7/1998 | Lippincott |
| 6,021,172 A | 2/2000 | Fossum et al. |
| 6,088,058 A | 7/2000 | Mead et al. |
| 6,242,227 B1 | 6/2001 | Lin et al. |
| 6,272,269 B1 | 8/2001 | Naum |
| 6,278,490 B1* | 8/2001 | Fukuda .................. H04N 5/235 348/362 |
| 6,331,156 B1 | 12/2001 | Haefele et al. |
| 6,464,633 B1 | 10/2002 | Hosoda et al. |
| 6,485,414 B1 | 11/2002 | Neuberger |
| 6,677,992 B1 | 1/2004 | Matsumoto et al. |
| 6,690,466 B2 | 2/2004 | Miller et al. |
| 6,692,431 B2 | 2/2004 | Kazakevich |
| 6,899,675 B2 | 5/2005 | Cline et al. |
| 6,921,920 B2 | 7/2005 | Kazakevich |
| 6,961,461 B2 | 11/2005 | MacKinnon et al. |
| 6,970,195 B1 | 11/2005 | Bidermann et al. |
| 6,977,733 B2 | 12/2005 | Denk et al. |
| 6,982,740 B2 | 1/2006 | Adair et al. |
| 6,999,118 B2 | 2/2006 | Suzuki |
| 7,037,259 B2 | 5/2006 | Hakamata et al. |
| 7,050,094 B2 | 5/2006 | Krymski |
| 7,079,178 B2 | 7/2006 | Hynecek |
| 7,102,682 B2 | 9/2006 | Baer |
| 7,106,377 B2 | 9/2006 | Bean et al. |
| 7,129,108 B2 | 10/2006 | Jang |
| 7,184,084 B2 | 2/2007 | Glenn |
| 7,189,226 B2 | 3/2007 | Auld et al. |
| 7,258,663 B2 | 8/2007 | Doguchi et al. |
| 7,319,478 B2 | 1/2008 | Dolt et al. |
| 7,356,198 B2 | 4/2008 | Chauville et al. |
| 7,522,341 B2 | 4/2009 | Mouli |
| 7,540,645 B2 | 6/2009 | Kazakevich |
| 7,544,163 B2 | 6/2009 | MacKinnon et al. |
| 7,545,434 B2 | 6/2009 | Bean et al. |
| 7,687,755 B2* | 3/2010 | Bae .................. H01L 27/14656 250/208.1 |
| 7,791,009 B2 | 9/2010 | Johnston et al. |
| 7,792,378 B2 | 9/2010 | Liege et al. |
| 7,794,394 B2 | 9/2010 | Frangioni |
| 7,813,538 B2 | 10/2010 | Carroll et al. |
| 7,830,434 B2 | 11/2010 | Li et al. |
| 8,089,542 B2 | 1/2012 | Chevallier |
| 8,100,826 B2 | 1/2012 | MacKinnon et al. |
| 8,101,903 B2 | 1/2012 | Mokhnatyuk |
| 8,144,226 B2 | 3/2012 | Shah et al. |
| 8,300,111 B2 | 10/2012 | Iwane |
| 8,537,241 B2 | 9/2013 | Ayers et al. |
| 8,559,743 B2 | 10/2013 | Liege et al. |
| 9,509,917 B2 | 11/2016 | Blanquart et al. |
| 2001/0019361 A1 | 9/2001 | Savoye |
| 2001/0030744 A1 | 10/2001 | Chang |
| 2005/0151866 A1 | 7/2005 | Ando et al. |
| 2005/0167602 A1 | 8/2005 | Dierickx |
| 2005/0234302 A1 | 10/2005 | MacKinnon et al. |
| 2005/0253176 A1 | 11/2005 | Pyo |
| 2006/0069314 A1 | 3/2006 | Farr |
| 2006/0202036 A1 | 9/2006 | Wang et al. |
| 2007/0285526 A1 | 12/2007 | Mann et al. |
| 2008/0045800 A2 | 2/2008 | Farr |
| 2008/0218598 A1 | 9/2008 | Harada et al. |
| 2009/0012361 A1 | 1/2009 | MacKinnon et al. |
| 2009/0160976 A1 | 6/2009 | Chen et al. |
| 2009/0292168 A1 | 11/2009 | Farr |
| 2010/0134662 A1 | 6/2010 | Bub |
| 2010/0165087 A1 | 7/2010 | Corso et al. |
| 2010/0182446 A1 | 7/2010 | Matsubayashi |
| 2010/0201797 A1 | 8/2010 | Shizukuishi et al. |
| 2011/0063483 A1* | 3/2011 | Rossi .................. H04N 5/3454 348/294 |
| 2011/0069189 A1 | 3/2011 | Venkataraman et al. |
| 2011/0122301 A1 | 5/2011 | Yamura et al. |
| 2011/0149358 A1 | 6/2011 | Cheng |
| 2011/0181840 A1 | 7/2011 | Cobb |
| 2011/0237882 A1 | 9/2011 | Saito |
| 2011/0237884 A1 | 9/2011 | Saito |
| 2012/0004768 A1 | 1/2012 | McDowall et al. |
| 2012/0041267 A1 | 2/2012 | Benning et al. |
| 2012/0050592 A1 | 3/2012 | Oguma |
| 2012/0078052 A1 | 3/2012 | Cheng |
| 2012/0120282 A1 | 3/2012 | Goris |
| 2012/0274811 A1 | 11/2012 | Bakin |
| 2013/0144120 A1 | 6/2013 | Yamazaki |
| 2017/0078548 A1 | 3/2017 | Blanquart et al. |

FOREIGN PATENT DOCUMENTS

| | | |
|---|---|---|
| JP | 2006-237772 B2 | 9/2006 |
| JP | 2006-523074 A | 10/2006 |
| JP | 2007-214832 B2 | 8/2007 |
| JP | 2007-215088 A | 8/2007 |
| JP | 2009-033316 A | 2/2009 |
| JP | 2010-278655 A | 12/2010 |
| JP | 2011-523538 A | 8/2011 |

OTHER PUBLICATIONS

Computer translation of JP 2006-237772.
Computer translation of JP 2006-523074.
Computer translation of JP 2007-214832.
Computer translation of JP 2007-215088.
Computer translation of JP 2009-033316.
Computer translation of JP 2010-278655.
Computer translation of JP 2011-523538.

* cited by examiner

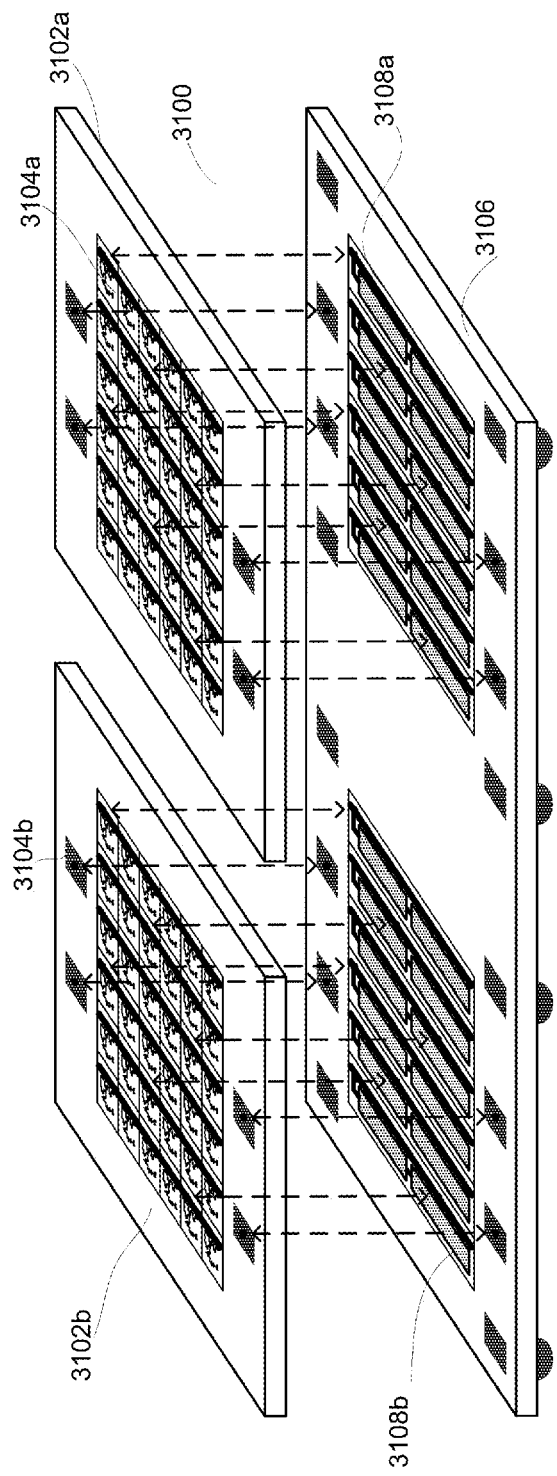
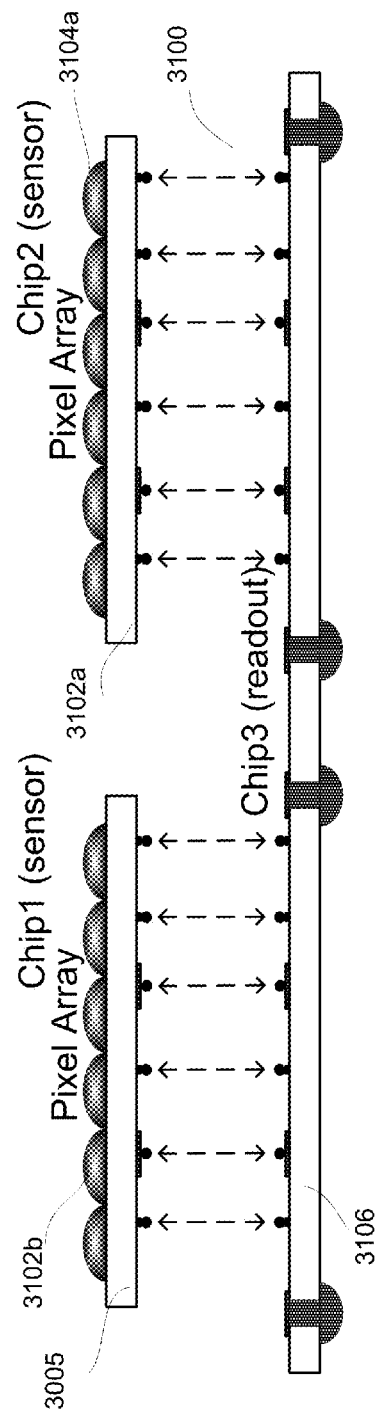
FIG. 28A
FIG. 28B

WIDE DYNAMIC RANGE USING MONOCHROMATIC SENSOR

CROSS-REFERENCE TO RELATED APPLICATIONS

This application is a continuation of U.S. patent application Ser. No. 15/362,512, file on Nov. 28, 2016 (U.S. Pat. No. 9,624,817, issued on Apr. 11, 2017), which application is a division of U.S. patent application Ser. No. 13/952,564, filed on Jul. 26, 2013 (U.S. Pat. No. 9,509,917, issued on Nov. 29, 2016), and claims the benefit of U.S. Provisional Patent Application No. 61/676,289, filed on Jul. 26, 2012, and U.S. Provisional Patent Application No. 61/790,719, filed on Mar. 15, 2013, and U.S. Provisional Patent Application No. 61/790,487, filed on Mar. 15, 2013, which are hereby incorporated by reference herein in their entireties, including but not limited to those portions that specifically appear hereinafter, the incorporation by reference being made with the following exception: In the event that any portion of the above-referenced applications are inconsistent with this application, this application supersedes said above-referenced applications.

BACKGROUND

Advances in technology have provided advances in imaging capabilities for medical use. One area that has enjoyed some of the most beneficial advances is that of endoscopic surgical procedures because of the advances in the components that make up an endoscope.

The disclosure relates generally to electromagnetic sensing and sensors related to increasing dynamic range within frames of an enhanced video stream. The features and advantages of the disclosure will be set forth in the description which follows, and in part will be apparent from the description, or may be learned by the practice of the disclosure without undue experimentation. The features and advantages of the disclosure may be realized and obtained by means of the instruments and combinations particularly pointed out in the appended claims.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with regard to the following description and accompanying drawings where:

FIGS. 28A and 28B illustrate a perspective view and a side view, respectively, of an implementation of an imaging sensor having a plurality of pixel arrays for producing a three dimensional image, wherein the plurality of pixel arrays and the image sensor are built on a plurality of substrates.

DETAILED DESCRIPTION

Figure 1:
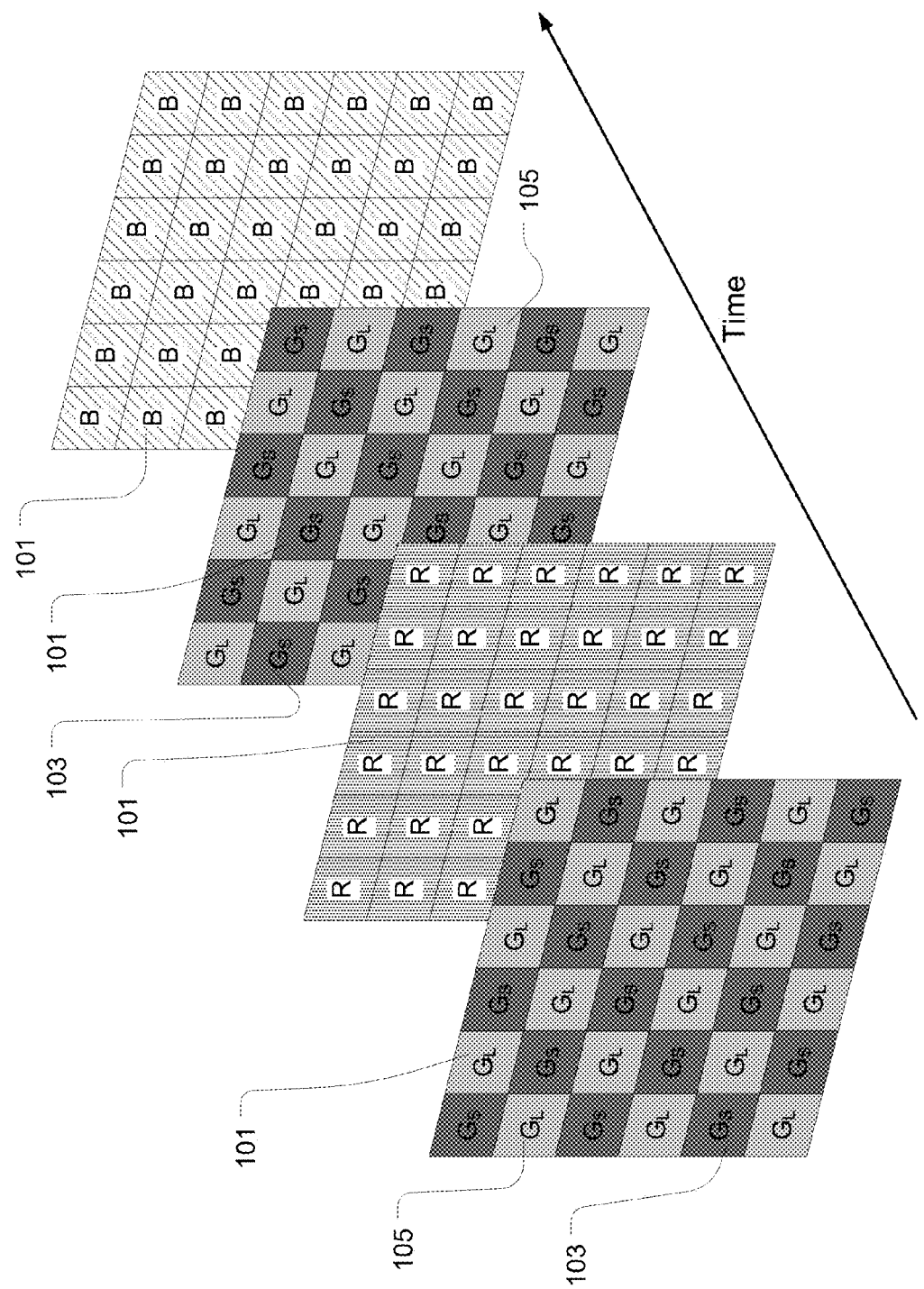
FIG. 1 illustrates an embodiment of a frame sequence pattern in accordance with the principles and teachings of the disclosure.

The disclosure extends to methods, systems, and computer based products for digital imaging that may be primarily suited to medical applications. In the following description of the disclosure, reference may be made to the accompanying drawings, which form a part hereof, and in which is shown by way of illustration specific implementations in which the disclosure may be practiced. It may be understood that other implementations may be utilized and structural changes may be made without departing from the scope of the disclosure.

As used herein, an emitter is a device that is capable of generating and emitting electromagnetic pulses. Various embodiments of emitters may be configured to emit pulses and have very specific frequencies or ranges of frequencies from within the entire electromagnetic spectrum. Pulses may comprise wavelengths from the visible and non-visible ranges. An emitter may be cycled on and off to produce a pulse or may produce a pulse with a shutter mechanism. An emitter may have variable power output levels or may be controlled with a secondary device such as an aperture or filter. An emitter may emit broad spectrum or full spectrum electromagnetic radiation that may produce pulses through color filtering or shuttering. An emitter may comprise a plurality of electromagnetic sources that act individually or in concert.

Dynamic range (DR) may be one of the most important characteristics of digital camera systems such as those employed in endoscopy or other applications. It governs the ability of the system to capture scenes with broad ranges of luminosity. Too small a DR and details within low light areas of the scene may be lost in the noise when the response of the system may be adjusted to accommodate for the bright areas. Conversely, if the system is adjusted to bring out the low-light detail, information in the bright areas may be lost because the signal exceeds the saturation level. DR may be defined as the ratio between the highest allowed signal, $S_{max}$, and the lowest resolvable signal. The latter may be conventionally equated to the overall read noise, $\sigma_R$, which arises from the analog readout process within the sensor:

$$DR = 20\log_{10}\left(\frac{S_{max}}{\sigma_R}\right)$$

Normally $S_{max}$, may be dictated by the charge capacity (i.e., the full-well) of the pixel. Many methods of artificially extending the DR have been invented, which include, e.g., dual exposures within the same frame, multiple frames with different exposures, logarithmic response pixels, dual response pixels and others. Each of them has its own benefits, shortcomings and limitations. In the case of dual exposure methods, the DR extension may be equal to the exposure time ratio ($T_{long}/T_{short}$), therefore:

$$DR = 20\log_{10}\left(\frac{S_{max}}{\sigma_R} \cdot \frac{T_{long}}{T_{short}}\right)$$

Such extensions of DR may be typically referred to as wide or high dynamic range (WDR, WiDy or HDR). In this system, the illumination of the scene may be provided by virtue of monochromatic fast light pulses, which may be synchronized to the frame captures by the image sensor. Each frame may receive a single wavelength of light or any combination of wavelengths, e.g., three. Since color modulation may be effected frame by frame, the sensor may be monochrome, which has a significant advantage for spatial resolution. The specific method of dual exposure described herein exploits the fact that the array may be monochrome in providing for the most granular and ideal spatial segmentation arrangement possible for two exposures; that of the checkerboard pattern.

Ultimately a final video sequence of full color frames at a certain frame rate may be generated. This will inevitably be a lower rate than the capture rate, since different components may be being derived from different captures.

Several possible checkerboard embodiments involve strobing each frame with one of three available monochromatic red, green and blue sources. Green information may be more valuable in regards to detail than blue and red, since the luminance perceived by the human eye peaks in the green region of the spectrum. For this reason, the popular Bayer pattern of color filters affords twice as many pixels to the detection of green light than either red or blue. For monochromatic frame sequencing then it may be advantageous to employ a repeating sequence of four frames, with two of the four being green, i.e., G-R-G-B. Green data may also be more important in regards to dynamic range since the rods in the human retina may be more sensitive at low light levels. Therefore, the dual exposure could be applied solely for the green frames. The most basic embodiment may configure half of the pixels to be short exposures on green frames and the other half may be configured as long exposures in the same way for every green frame.

Figure 2:
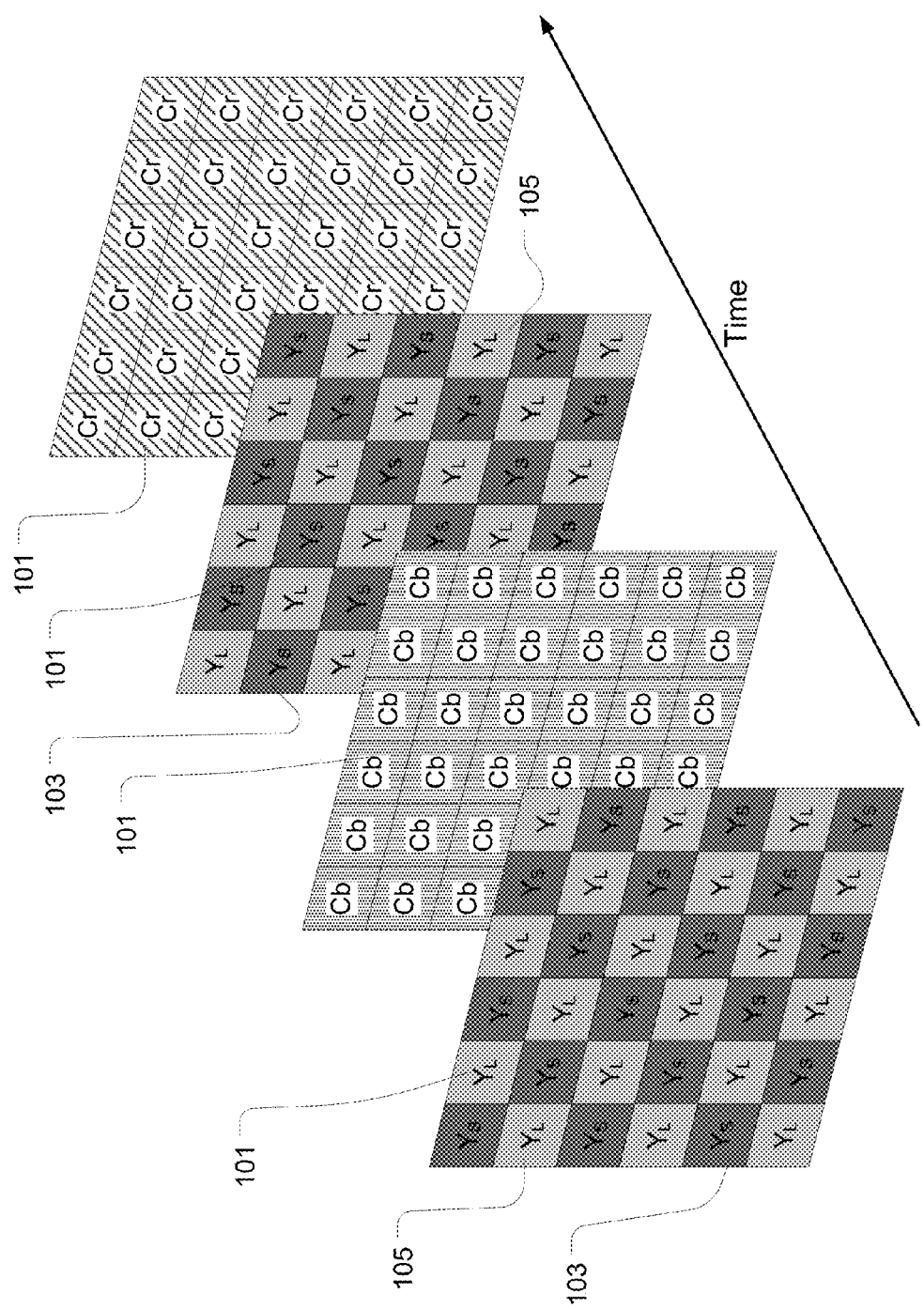
FIG. 2 illustrates an embodiment of a frame sequence pattern in accordance with the principles and teachings of the disclosure.

Referring now to FIG. 1, there is illustrated an advantageous embodiment that would alternate which particular subset of pixels 101 are configured as long exposures and which are configured as short exposures on successive green frames. This particular embodiment is illustrated in FIG. 1, in which the L and S subscripts indicate long and short exposures, respectively, with respect to green (G), red (R), and blue (B) frames, or other denoted color schemes in other figures. As illustrated in FIGS. 1 and 2, the short exposure pixels are indicated by 103 and the long exposure pixels are indicated by 105. Such an approach may offer an advantage for perceived resolution since the interpolated locations continually swap places with actual pixel samples for a given exposure, from frame to frame.

It will be appreciated that other ways of utilizing pulsed monochromatic light sources may be possible. Co-pending U.S. patent application Ser. No. 13/952,518 entitled CONTINUOUS VIDEO IN A LIGHT DEFICIENT ENVIRONMENT is hereby incorporated by this reference into this disclosure as if fully set forth herein. One particularly advantageous way may be to provide pure luminance (Y)

information by pulsing the red, green and blue sources at the same with the appropriate pulse energy proportions. The chrominance-red (Cr) and chrominance-blue (Cb) information can be provided on the alternate frames by adding sufficient luminance in each case to make all of the pulse energies positive. The image processing chain can extract the data in a true color space provided it knows the applied proportions. In such a circumstance, the dual exposure may be applied on the luminance frames where it may be most needed, as indicated in FIG. 2.

Figure 3:
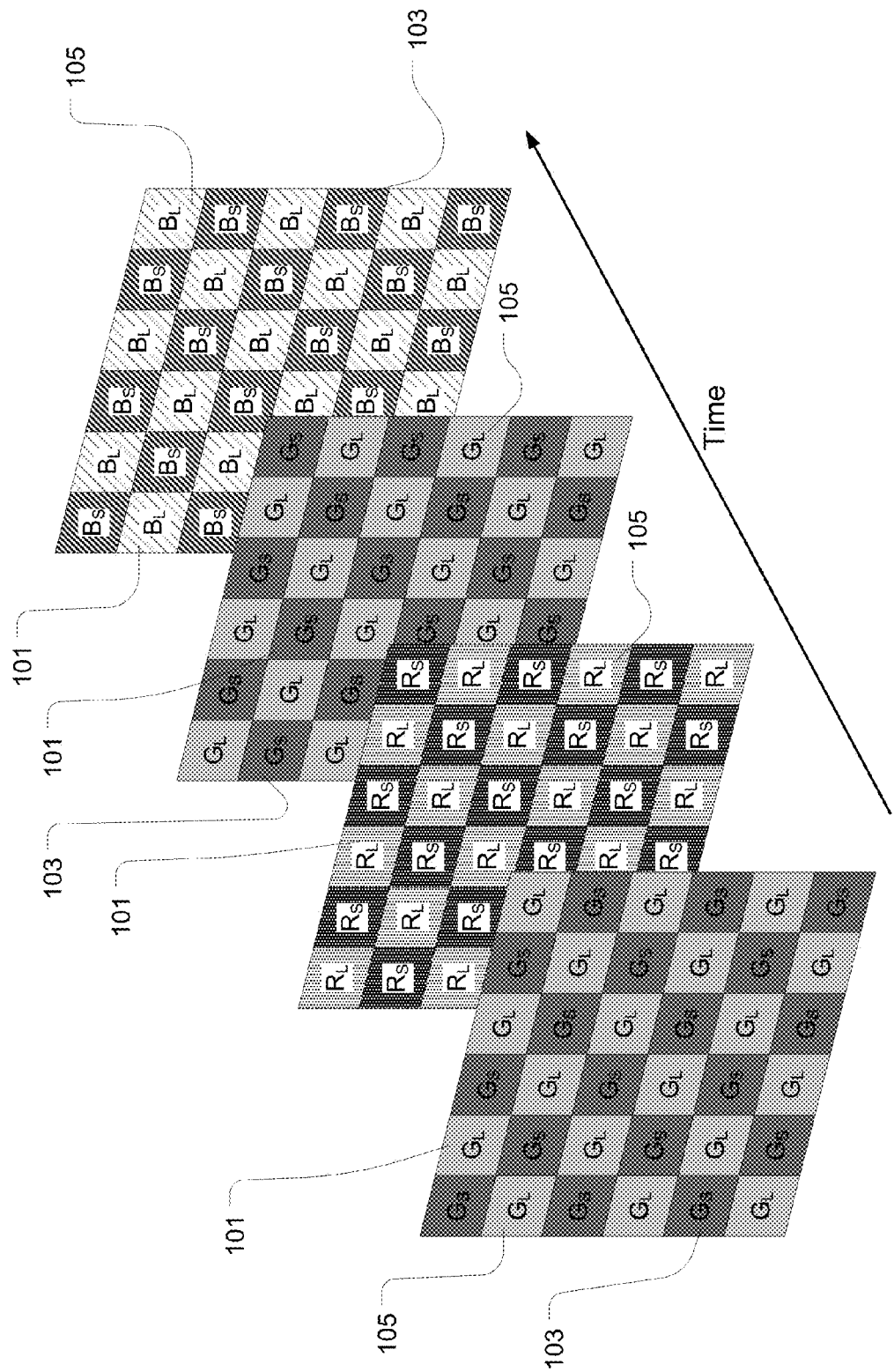
FIG. 3 illustrates an embodiment of a frame sequence pattern in accordance with the principles and teachings of the disclosure.
Figure 4:
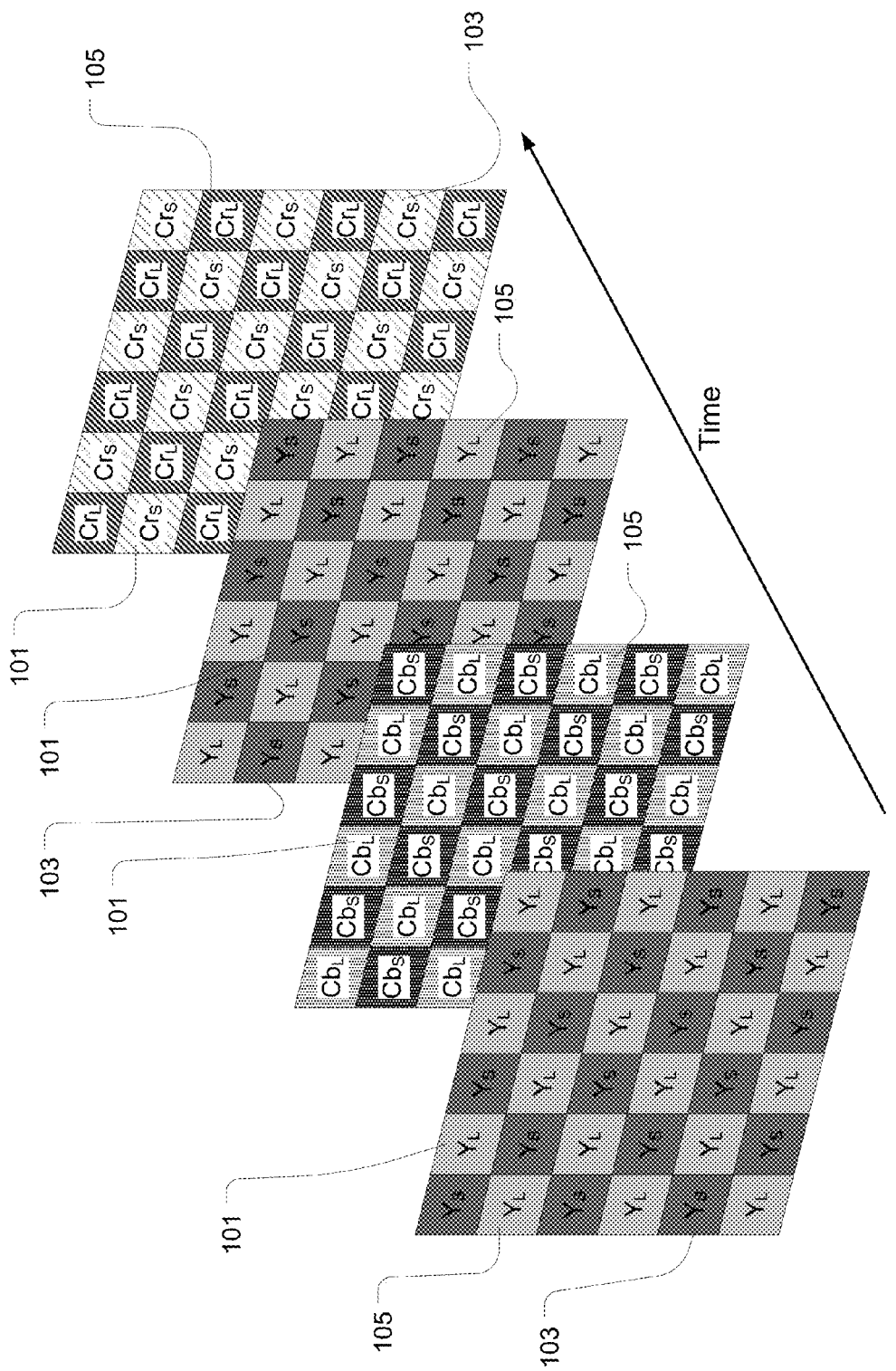
FIG. 4 illustrates an embodiment of a frame sequence pattern in accordance with the principles and teachings of the disclosure.

The application of dual exposure sampling may not be limited to the green or luminance frames and should the circumstances in the scene warrant it, another embodiment may also have independent dual exposure ratios applied for the red and blue frames, as illustrated in FIG. 3. FIG. 4 shows the equivalent case for luminance-chrominance light pulsing.

Figure 5:
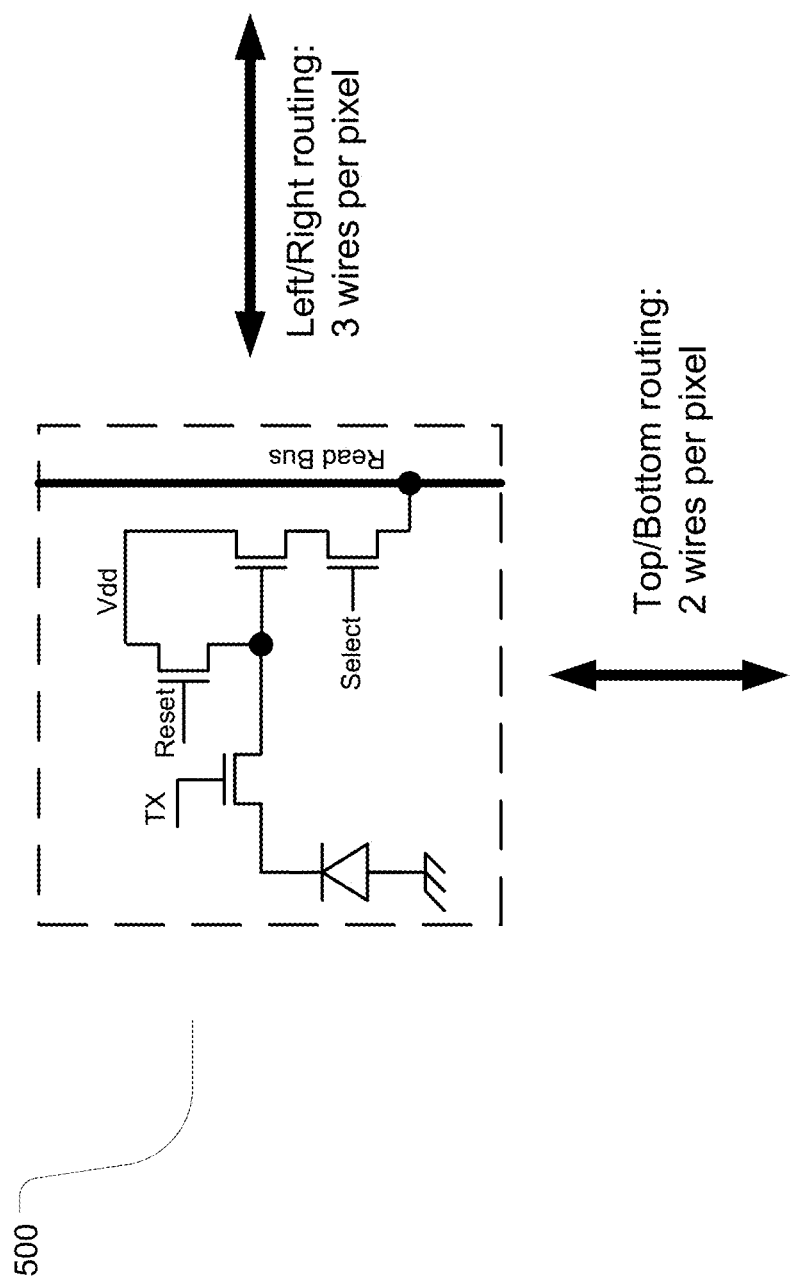
FIG. 5 illustrates a schematic representation of an embodiment of a pixel in accordance with the principles and teaching of the disclosure.

FIG. 5 shows a circuit diagram for a conventional unshared pixel 500 having the four transistors necessary to facilitate low-noise, correlated double sampling. There may be five service wires required to operate the pixel 500, as shown. It may be possible to share three of the four transistors between two or more neighboring pixels 500, which increases the available area for the photodiode. As pixel size may be reduced it becomes harder to maintain quantum efficiency since the photodiode occupies a smaller proportion of the area. Sharing may be an approach that may be commonly used by sensor manufacturers, particularly for small pixel devices. Another benefit afforded by transistor sharing may be a reduction in the average number of wires required per pixel.

Figure 6:
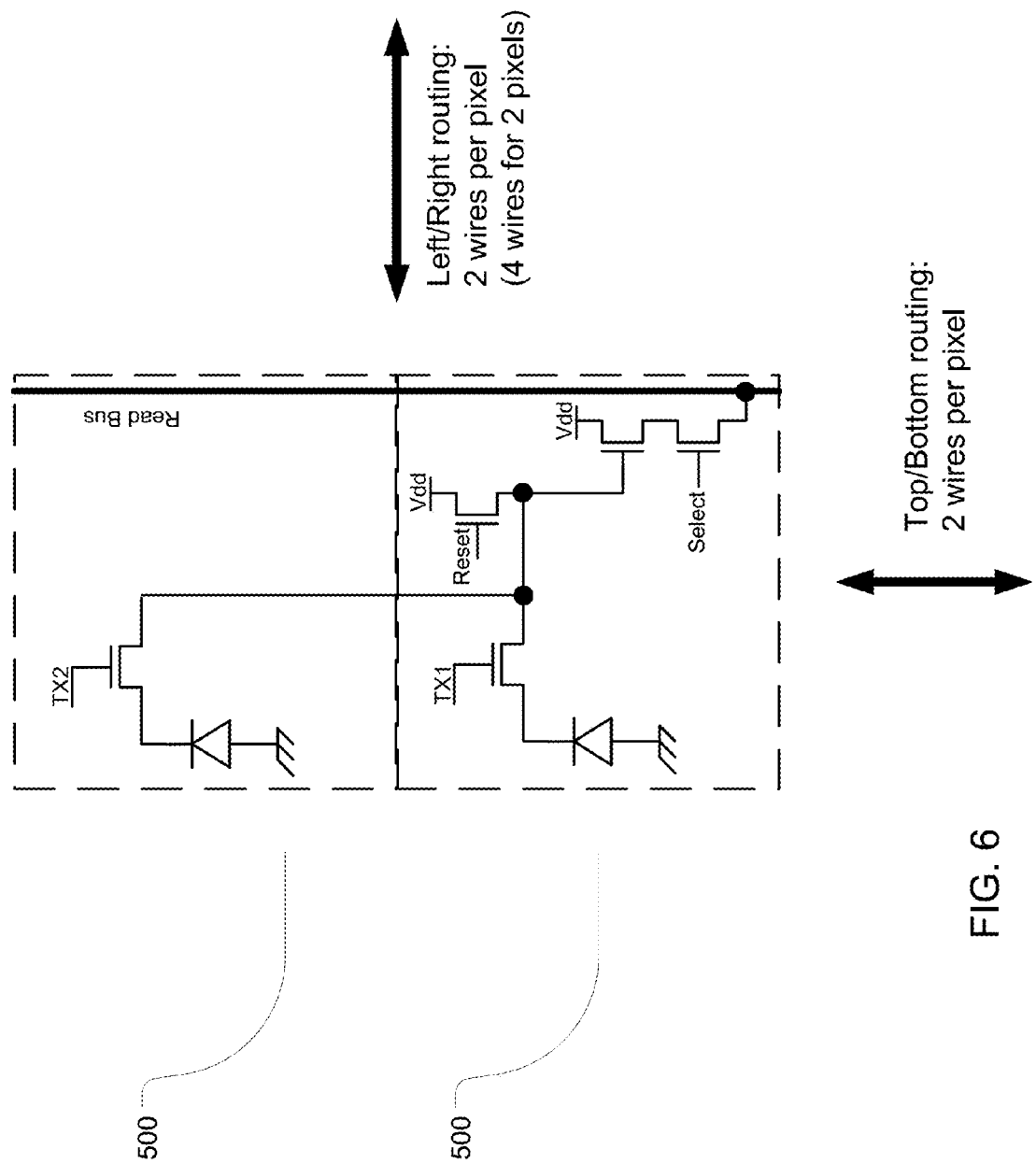
FIG. 6 illustrates a schematic representation of an embodiment of a shared pixel configuration in accordance with the principles and teaching of the disclosure.

FIG. 6 depicts the unit cell for an array with conventional 2-way vertical sharing. Since three transistors may be shared, there may be five transistors total for two pixels, i.e. 2.5 transistors per pixel. In regards to wire routing, six wires in total may be needed per pixel pair. Four of them may be horizontally routed and two of them may be vertically routed, resulting in two per pixel edge in each dimension. This may be in contrast with the unshared case which has three horizontal and two vertical wires per pixel edge.

Figure 7:
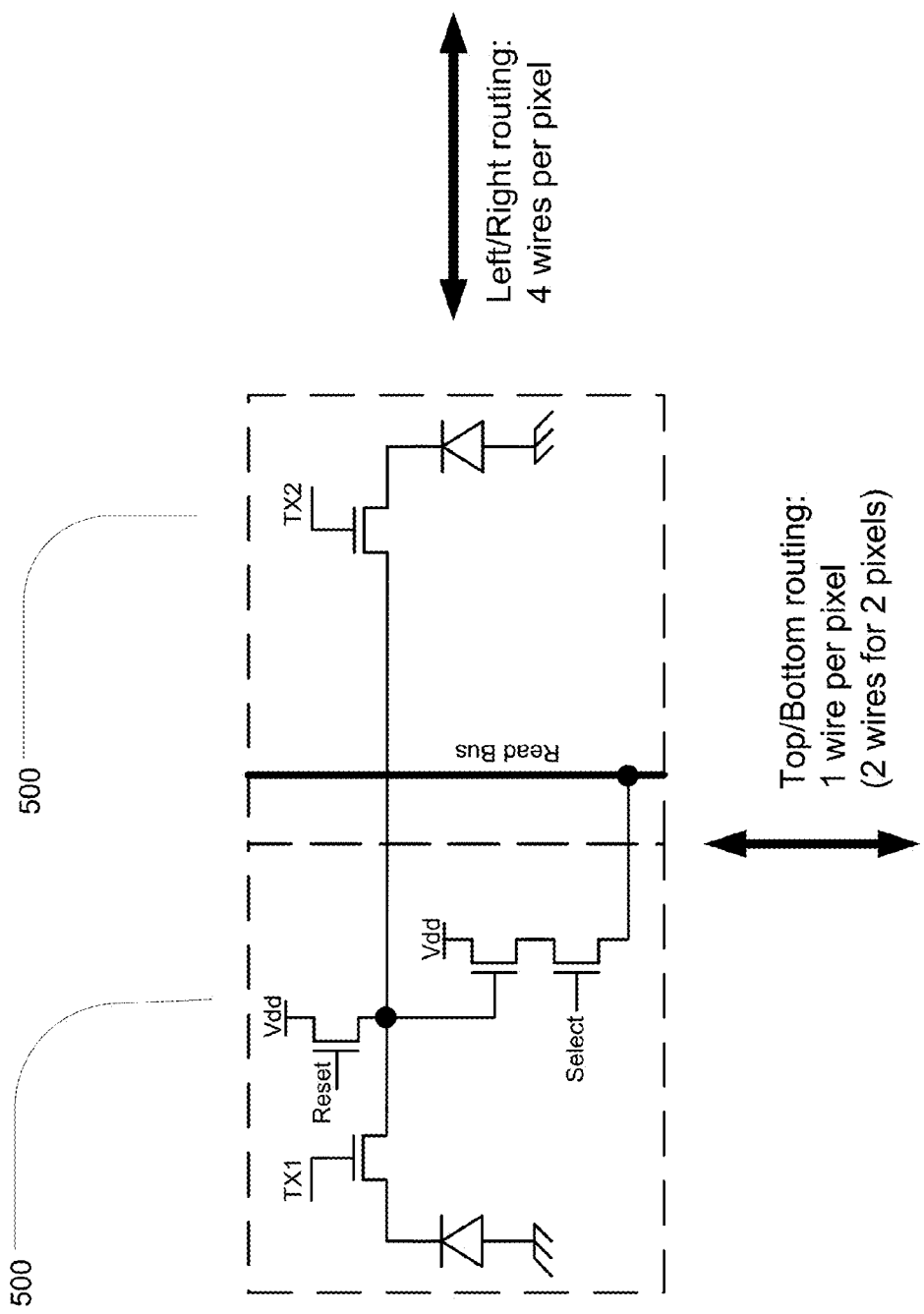
FIG. 7 illustrates a schematic representation of an embodiment of a shared pixel configuration in accordance with the principles and teaching of the disclosure.

The approach may be to pair up the pixels horizontally instead of vertically. This may be normally less favorable as regards wire routing simplicity, since the four horizontal wires now may be fit in a single pixel edge. See FIG. 7. There may be two significant benefits however, that outweigh this routing disadvantage.

Figure 8:
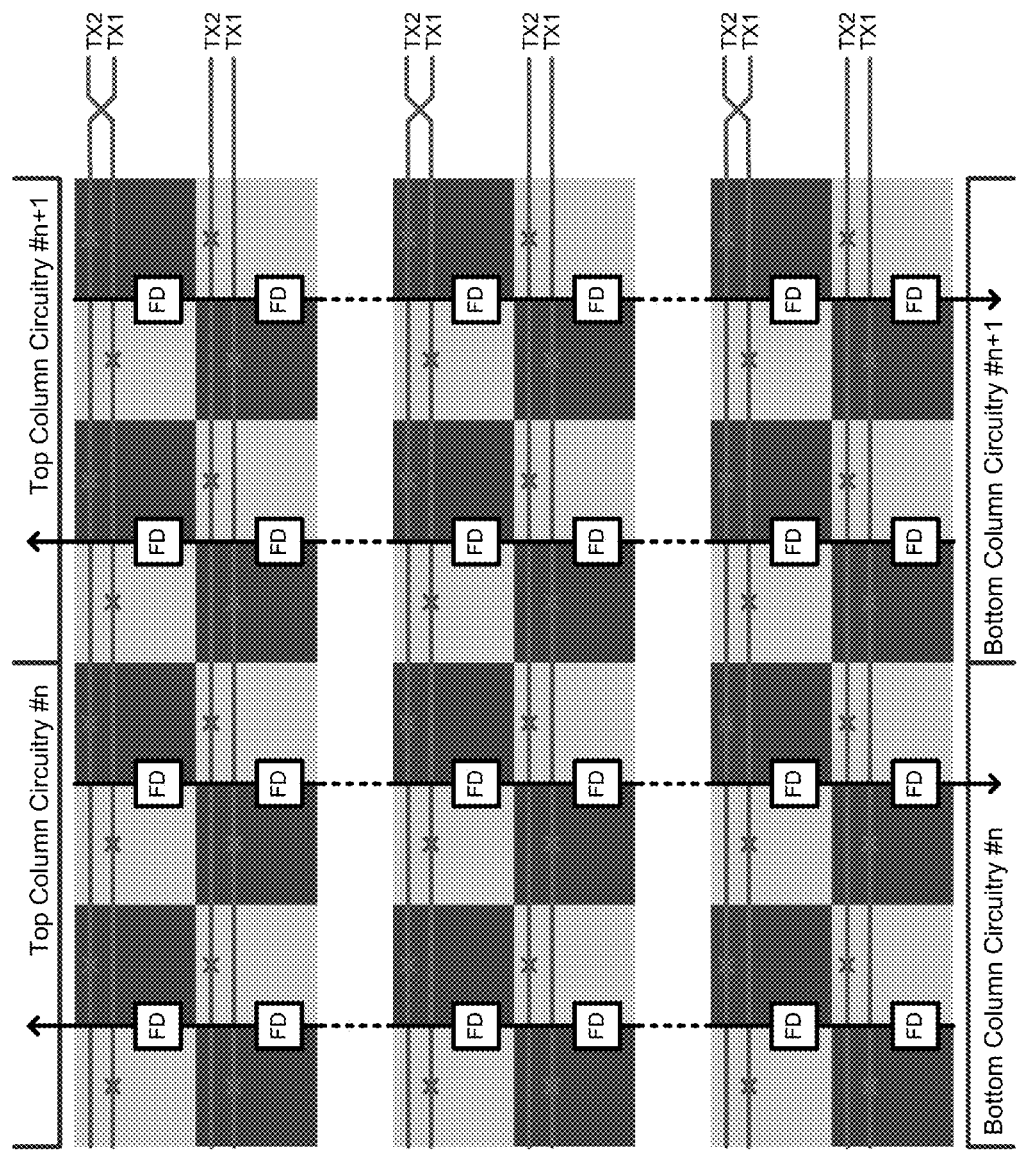
FIG. 8 illustrates a schematic representation of an embodiment of a pixel array having a plurality of pixels having differing sensitivities in accordance with the principles and teaching of the disclosure.

The first benefit may be that only half of the net circuitry may be required to service each column. This helps to reduce the overall chip area since the column circuitry may be a major consumer of chip space. As illustrated in FIG. 8, a single column circuit may serve four columns of pixels instead of two, which would be the case for vertical 2-way sharing.

The second benefit may be that horizontal sharing provides two independent TX signals per row. This opens up the possibility of having two independent exposures within a single row, which alternates between odd and even columns, as shown in FIG. 8. The checkerboard arrangement of dual exposures may be made possible now by virtue of switching the TX1 and TX2 odd/even column associations, on alternate rows. FIG. 8 indicates how this may be done for one embodiment by inserting a "twist" in the TX1/TX2 routing for every second row. This type of odd-even exposure pattern may be only applicable for the case of monochrome sensors. Color sensors have neighboring pixels with different color filters therefore odd/even exposure modulation would only be effective in changing the white balance and not in increasing the dynamic range.

In other embodiments, the switching of the TX1/TX2 assignments from row to row may be accomplished by virtue of two alternating flavors of row driver circuitry at the side of the array, or by crafting the TX1/TX2 routing differently within the odd and even rows.

Figure 9:
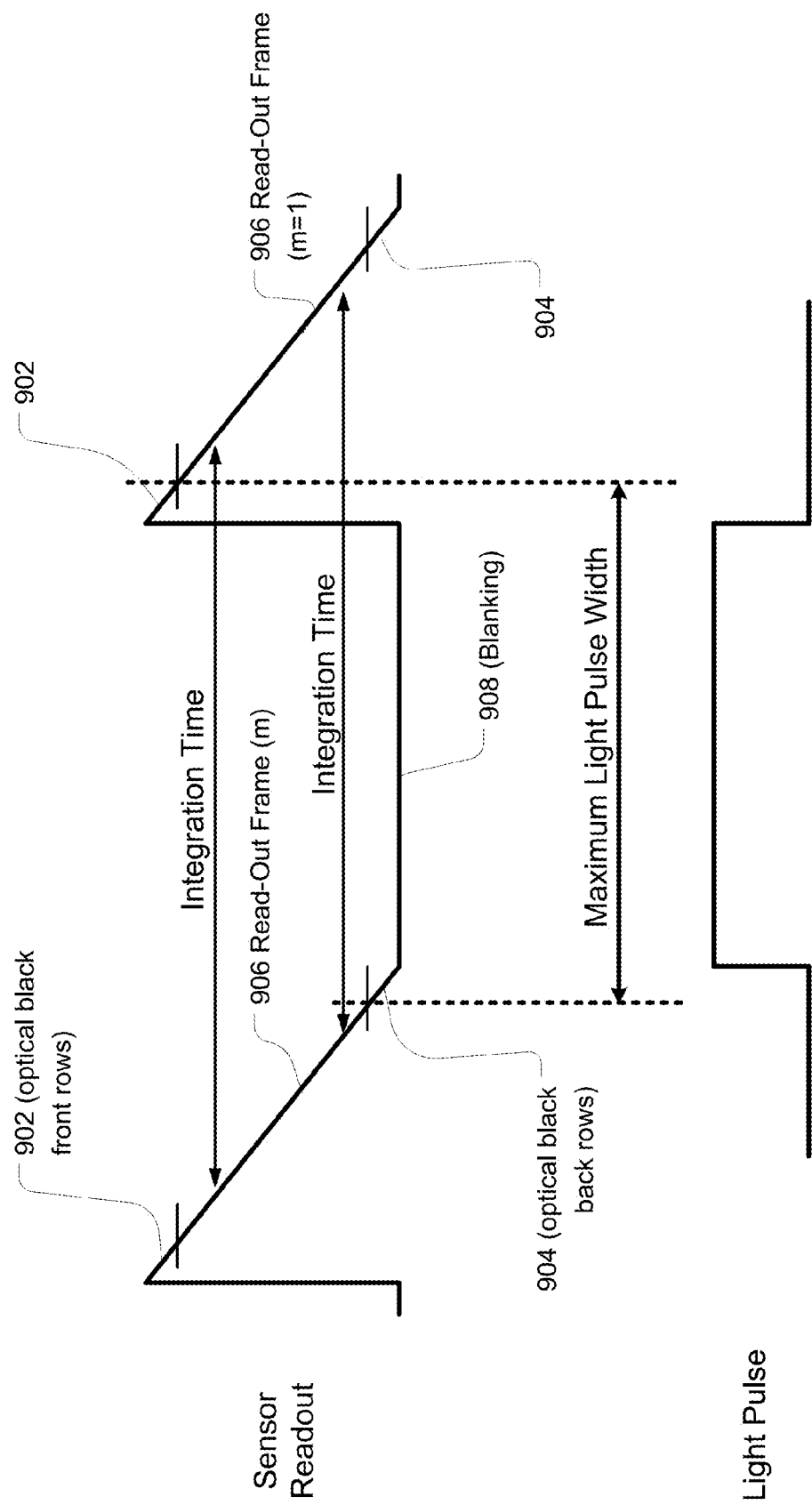
FIG. 9 illustrates a graphical representation of the operation of a pixel array in accordance with the principles and teachings of the disclosure.

Referring now to FIG. 9, there is depicted the general timing situation for a rolling shutter CMOS sensor with full-frame integration. In the figure, the diagonal lines represent the action of the read and reset pointer as it rolls through the rows of pixels. This period includes the time during which optical black or optically blind (OB) rows 902 (both front and back rows) may be read (e.g., during the read out frame 906), blanking time 908 and the time during which any other data that may not be physical pixel data may be issued (e.g., service line time).

The philosophy of modulating the light color on a frame-by-frame basis may be so that the sensor may be monochrome and thus have higher resolution than, e.g., a Bayer based equivalent. The penalty may be that multiple frames may be read in order to produce a single full color image. This penalty may be nullified and the frame rate restored, however, if the sensor is able to be read out correspondingly faster.

Figure 10:
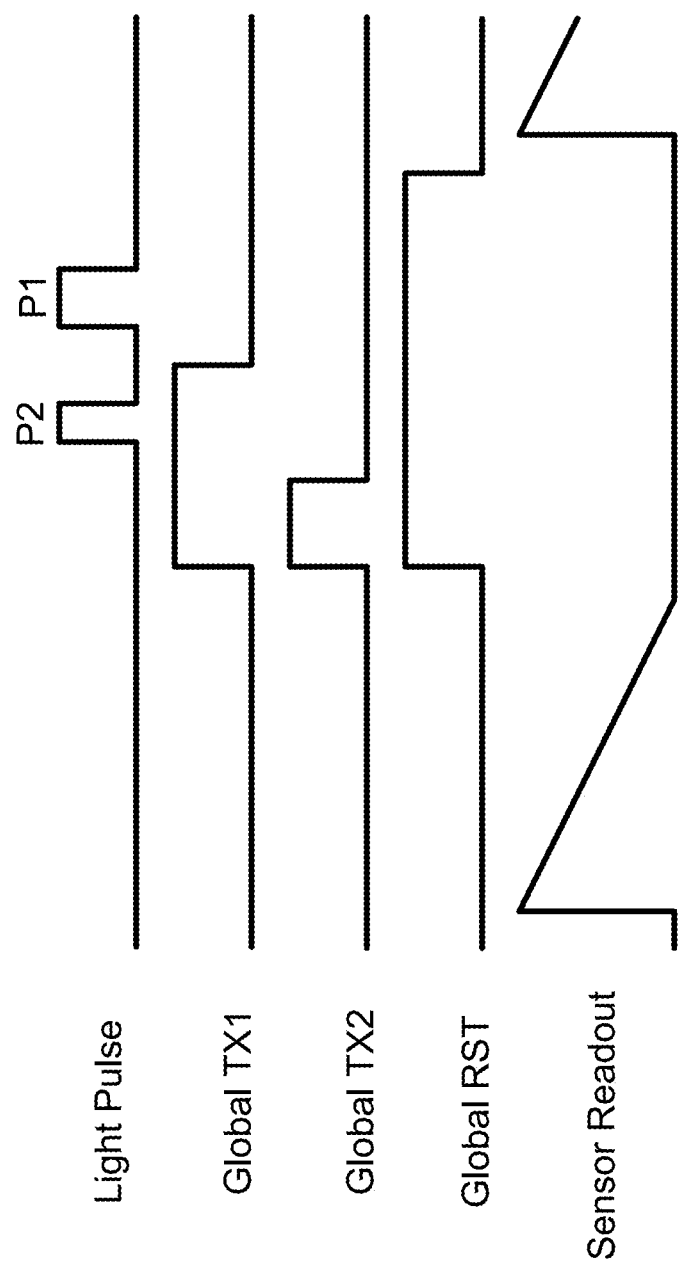
FIG. 10 illustrates a graphical representation of the operation of a pixel array in accordance with the principles and teachings of the disclosure.
Figure 11:
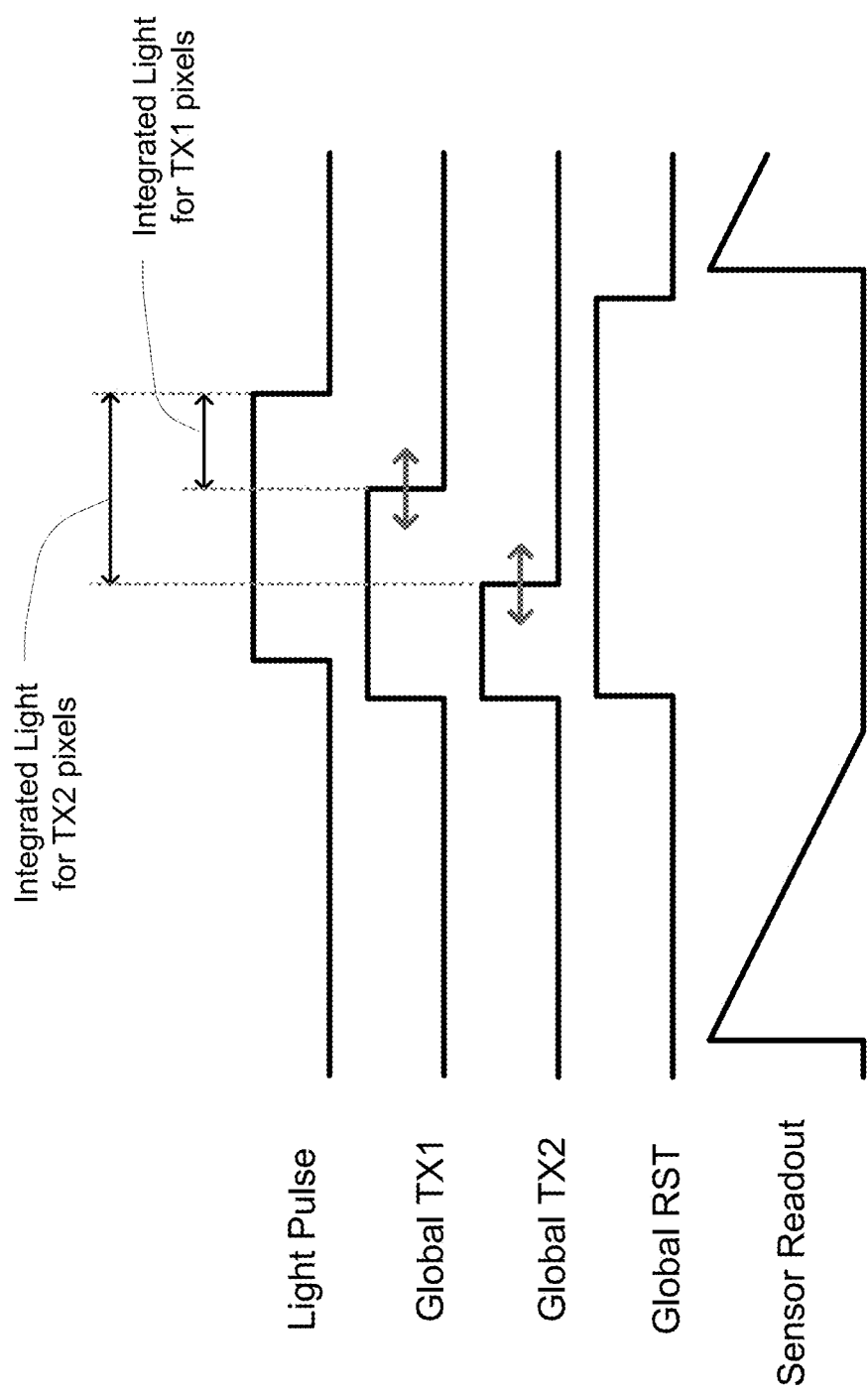
FIG. 11 illustrates a graphical representation of the operation of a pixel array in accordance with the principles and teachings of the disclosure.

FIGS. 10 and 11 illustrate the timing for two alternative ways in which multiple sets of pixels in an array may integrate different degrees of light. The exposure modulation may be effected by virtue of two global TX pulses, GlobalTX1 and GlobalTX2. They effectively create two global shutters when combined with the light pulse edge(s).

At the end of the integration period, the rolling pointer provides another TX pulse in order to transfer the signal for readout. For descriptive purposes, the case of two sets of pixels of different exposures in the checkerboard pattern (as described above), will mainly be emphasized. It should be noted however, that the scope of this disclosure is intended to cover cases with higher numbers of pixel types (i.e., exposures) and with alternative physical pixel type arrangements. The spatial pattern depends on the number of pixel sets, the pixel layout, the pixel array arrangement and the pixel array connections to the peripheral circuitry.

To avoid confusion the rolling TX signals may be referred to here as TX1 and TX2, whereas the global TX signals may be called GlobalTX1 and GlobalTX2. Global pulses affect all attached pixels in the array at the same time. The non-global pulses may be applied via the rolling pointer.

Those knowledgeable of CMOS image sensors should note that this method of global shutter does not suffer from the problems associated with global shutter when used with continuous illumination. In that case, the signals may be stored on the leaky floating diffusion nodes for significant periods of time, whereas for the two methods described herein with pulsed illumination, the benefit may be taken of the photodiode to store the photosignal.

Note that pixels may be held in reset as long as their transfer (TX) and reset (RST) transistors may be held on (i.e., the high state in the Figures). In that state any current in the photodiode may be drained off to the supply.

The integration period starts when the TX transistor turns off (low in the Figures). Now referring to FIG. 10, all pixels may be held in reset mode and may be therefore flushed, when GlobalTX1, GlobalTX2 and GlobalRST may be all high. When GlobalTX2 goes low, all pixels in the array attached to TX2 start to integrate. When the P2 light pulse occurs, its corresponding photocharge may be integrated by the TX2 pixels. However, because the GlobalRST and GlobalTX1 signals may be still high, any photocharge created by the P2 pulse in the TX1 pixels may be just drained off. When GlobalTX1 goes low, the TX1 pixels start to integrate. At that point, the TX2 pixels will have fully integrated the P2 pulse and the TX1 pixels, nothing. When the P1 light pulse occurs, it may be integrated by both the TX1 and the TX2 pixels. Therefore at the end of the sequence, the TX1 pixels will have a net photocharge resulting from only the P1 light pulses whereas the TX2 pixels will have integrated both light pulses.

FIG. 11 may be a similar timing diagram, for an alternative dual illumination embodiment. Instead of instigating 2 separate discrete light pulses, a single light pulse stays on during the period that both TX transistors may be turned off. The integrated light may be proportional to the time between the TX falling edge and the light pulse falling edge, therefore different pixel responses may be achieved by staggering the GlobalTX1 and GlobalTX2 falling edges. For the example shown, the TX1 pixels integrate ~⅓ of the light generated by the light pulse whereas the TX2 pixels integrate ~⅔ of the total pulse energy.

In a further embodiment, the dual illumination can be achieved with a mixture of the FIG. 10 and FIG. 11 timings. The GlobalTX2 signal would return to its low state before the rising edge of the single light pulse, which would make the TX2 pixels integrate the whole energy of the light pulse.

The dual exposure in this case may be achieved by the different timings described with respect to FIGS. 10 and 11, where a greater number of illuminations can be achieved by increasing the number of light pulses during the same blanking time.

Figure 12:
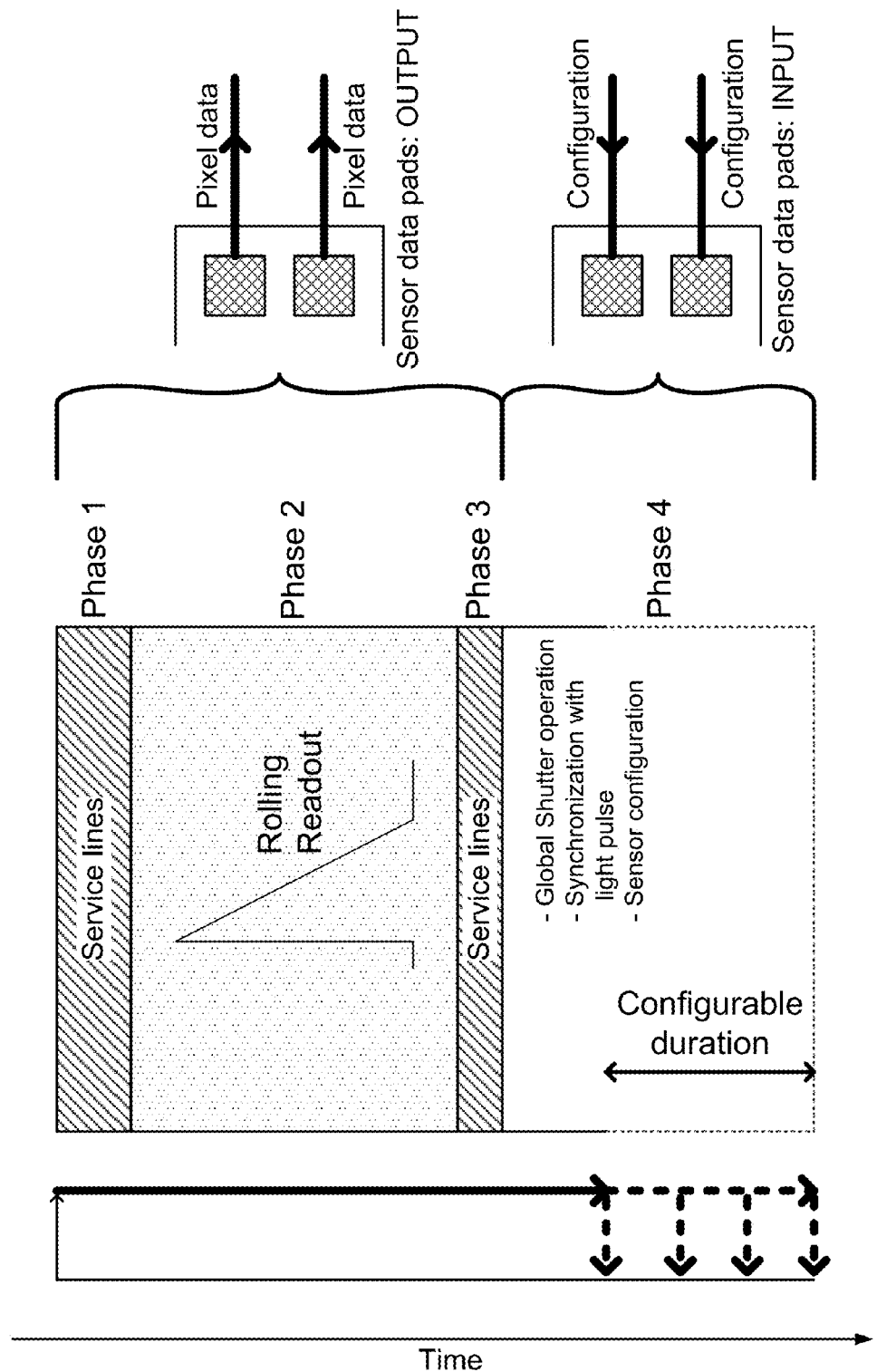
FIG. 12 illustrates a graphical representation of the operation of a pixel array over time in accordance with the principles and teachings of the disclosure.

FIG. 12 shows the internal timing of an embodiment of a minimal area custom sensor, for the purpose of endoscopic imaging in the presence of controlled, pulsed illumination. Each frame period may comprise four distinct phases, which may be optimized for monochrome light pulsing and multiple pixel illuminations. During phases 1 and 3, data may be issued from the sensor, which may be not signal samples from physical pixels. Rather they may be data concerned with the synchronization of the chip to the camera system and for data locking. These "service line" periods may also be used for internal and external monitoring and for the encoding of certain types of non-pixel data within the line. Such internal monitoring may include the sensor temperature, plus certain voltages and currents. External monitoring may include hand-piece button activity or, e.g., data from measurements of the angle of the endoscope. Phase 2 may be concerned with the sensor rolling readout (internal timing and synchronization) while phase 4 may be for the purpose of sensor configuration. During the configuration phase, the sensor output data lines may be reversed to accept incoming configuration commands. Therefore the camera controller may be synchronized to the phase 4 period. Phase 4 also doubles as the global shutter phase during which the operations depicted in FIGS. 10 and 11 may be performed. For this reason, phase 4 may be also synchronized with the light pulsing system.

Figure 13:
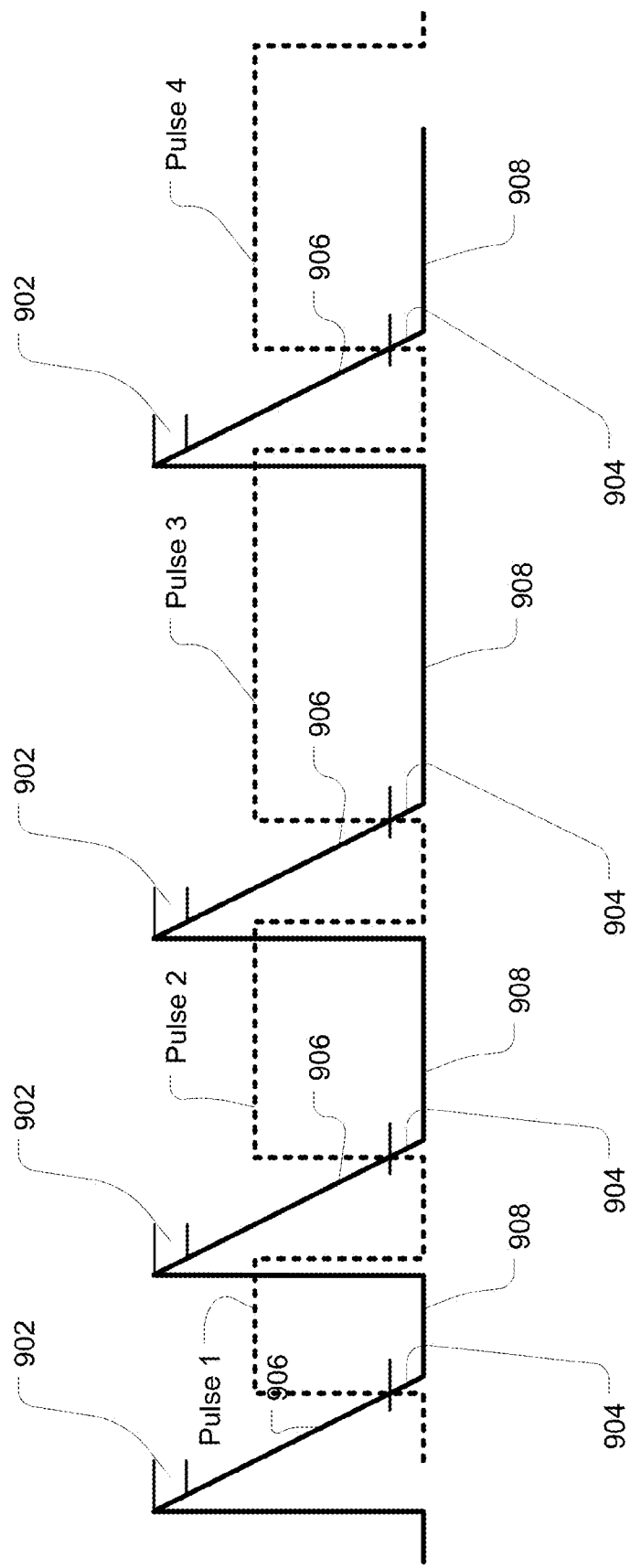
FIG. 13 illustrates a graphical representation of the operation of a pixel array over time in accordance with the principles and teachings of the disclosure.

Note that the pulse widths and timing of the global signals (GlobalTX1, GlobalTX2 and GlobalRST) may be fully programmable and that phase 4 may be the only phase with variable length. This enables the available pulse time to be tuned in order to match the available light power, given the type of frame it is. Individual wavelength sources may vary significantly, e.g., in regards to maximum available light power, quantum efficiency and response time. What may be important may be that the final frame rate may be a suitable multiple of the average capture rate. Beyond that, any variation within the repeating pattern of frame types can be taken care of by the appropriate buffering within the image signal processing chain (ISP). FIG. 13 illustrates an example of a 4-frame cycle with four different frame lengths and the four different blanking times accepting four maximum-allowed light modulations.

Figure 14:
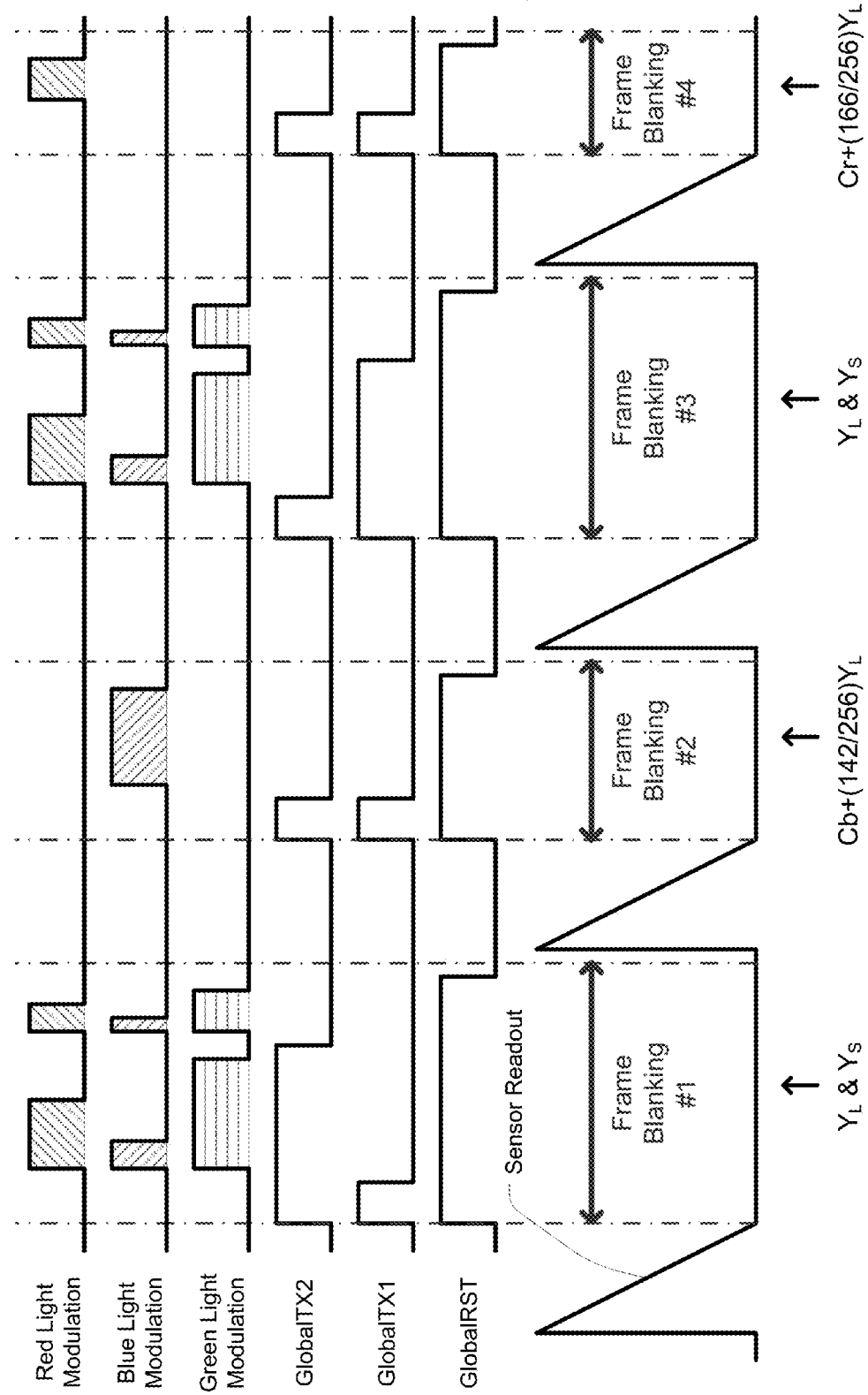
FIG. 14 illustrates a graphical representation of the operation of a pixel array over time in accordance with the principles and teachings of the disclosure.

FIG. 14 shows the timing diagram for the frame sequence illustrated in FIG. 2, which may be based upon the Y-Cb-Y-Cr pattern. All three sources may be fired during the luminance frames, i.e. frames #1 and #3. Frames #2 and #4 may be able to provide the Cb and Cr information respectively with a single wavelength pulse, by virtue of a critically tuned admixture of luminance.

Another approach to dynamic range enhancement may be provided by spatial binning of signals. An additional advantage of having a monochrome sensor may be that neighboring pixels may be binned together. Binning enables a greater reach of signal and thus greater DR, at the expense of spatial resolution.

Precisely where the binning takes place, dictates the effectiveness of binning in extending the DR. Take for example binning of two adjacent pixels, (2-way binning). If the binning may be done in the digital domain, an additional factor 2 (6 dB) of signal may be realized. However there may be two analog samples, each contributing an equal amount of read noise which amounts to a factor √2 (3 dB) of noise enhancement. Therefore the binning of data from two pixels at a point later in the chain than the source of read-noise amounts to 3 dB of additional DR. However, if the binning may be performed in the charge domain, i.e., at the pixel level as described earlier, then the additional DR that may be realized may be 6 dB, since the addition of readout noise occurs after the summation of signal.

The 2-way shared architecture described earlier provides for just such a means of 2-way binning in the charge domain. Simultaneous pulsing of the TX1 and TX2 signals results in both photo-signals being transferred to the shared floating diffusion at the same time. When each row may be subsequently read out, it has twice the charge range with the same noise, as compared to the un-binned case, and therefore 6 dB of extra DR.

An embodiment may comprise dual exposure control. The key to optimal, effective operation of this type of dynamic range (DR) enhancement (i.e., dual exposure) may be continuous control over the exposure time ratio.

In particular: first there should be no dynamic range extension at all, if the scene does not demand it, i.e., if the dynamic range of the scene may be below the intrinsic dynamic range of the pixel. Second, if the dynamic range of the scene may be greater than the pixel, the amount of added dynamic range should be just sufficient to provide for it with minimal margin.

The reason for this may be that artificial dynamic range extension always comes at a price. For the method described in this disclosure, there may be a spatial resolution cost, which increases on a sliding scale with increasing exposure ratio. In the limit of maximal exposure ratio, the vast majority of the useful image content, for either high or low luminosity scene regions, comes from only one of the exposures. At that extreme, the resolution asymptotically approaches the equivalent of having liNE, times the number of pixels in x and y and then up-scaling by interpolation. At the other extreme, when the ratio may be unity, there may be no DR extension and no penalty.

Figure 15:
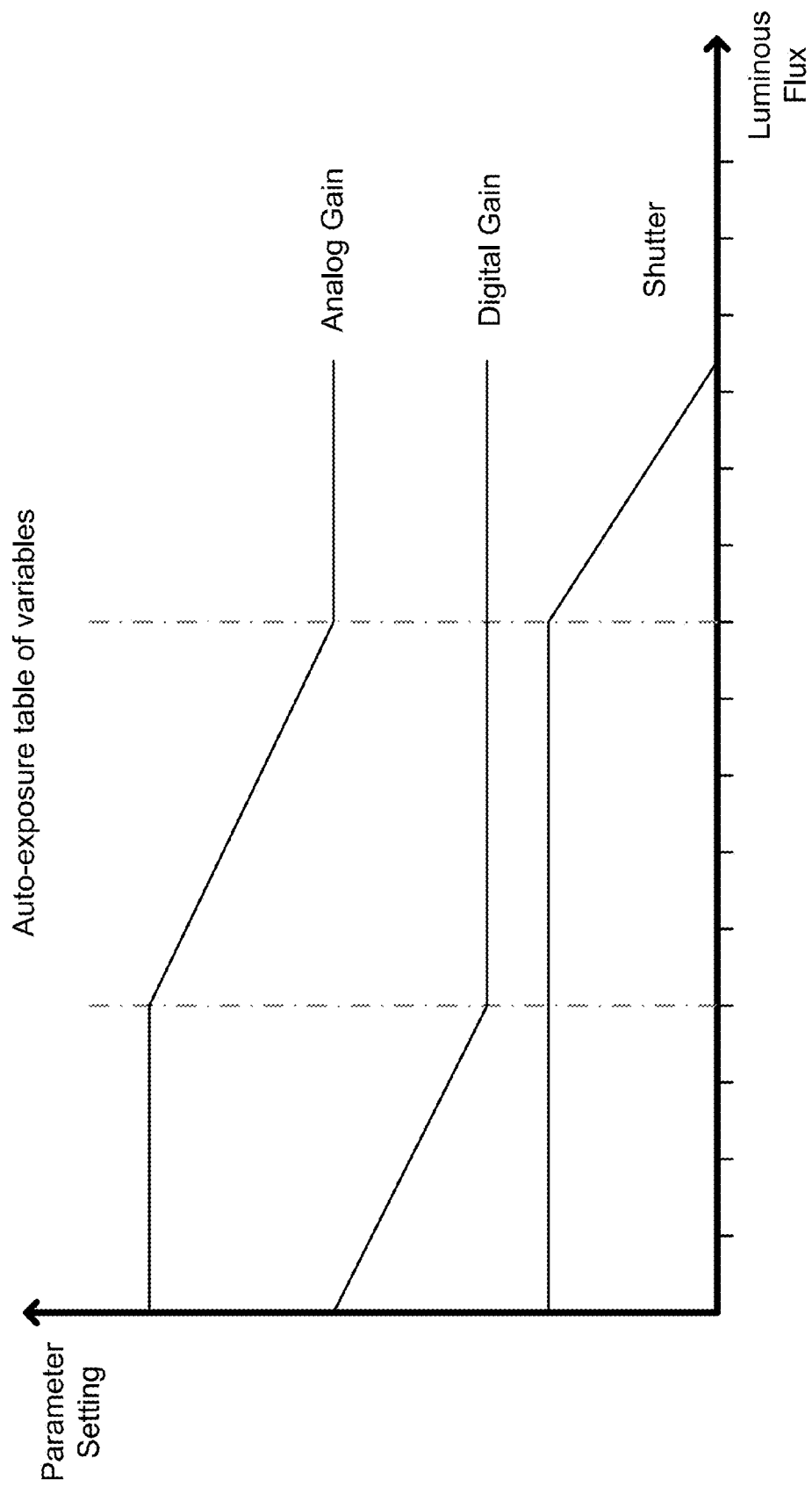
FIG. 15 illustrates a graphical representation of the operation of a pixel array over time in accordance with the principles and teachings of the disclosure.

Generally, digital cameras that experience randomly varying illumination scenarios, such as camcorders, incorporate a means of continually adjusting the sensor operation conditions so as to always make the best use of the available DR. This process may be known as auto-exposure. There may be typically several variables that may be adjusted according to a pre-defined table, including, e.g., integration time (shutter), analog gain, digital gain, aperture etc. FIG. 15 is an example of a hypothetical table for a system that incorporates shutter time, analog gain and digital gain. The lighting itself may be normally beyond the control of the camera with the exception of flash illumination used for still capture.

This disclosure may be specifically concerned with a camera system that has full control over the amount of pulsed red, green and blue illumination, frame by frame, for continuous video capture.

In the case of such a pulsed illumination system, the scene illuminance may be under the control of the camera or imaging device. Therefore the overall light pulse energy effectively takes the place of the shutter. Since more photosignal results in higher SNR, the light energy may be increased until the desired digital signal level may be reached within the ISP chain, for a chosen percentile of the distribution of a selected central region of pixels. The analog gain may be held at its minimum setting which can be considered to be the gain at which the bottom of the distribution of pixel signal capacity (full well), may be just above the upper rail of the ADC, (with some contingency for sensor to sensor variation). The maximum light pulse energy may be limited by the duration of the available portion of the frame and by the maximum electromagnetic energy provided, e.g., by laser diode or LED current. Only when that limit may be reached may be any gain applied. For the R-G-B-G pulse sequence case, the best overall SNR may be obtained by monitoring and controlling the three frame types independently, (so as to maximize all photon fluxes) and attenuating two of the colors digitally in the ISP for white balance purposes. An alternative approach to white balance may be to modulate the relative R, G and B pulse energies. This approach has lower final signal over noise ratio (SNR), but it still eliminates the need for any digital white balance gains that may be greater than unity, which would enhance the perception of noise.

Figure 16:
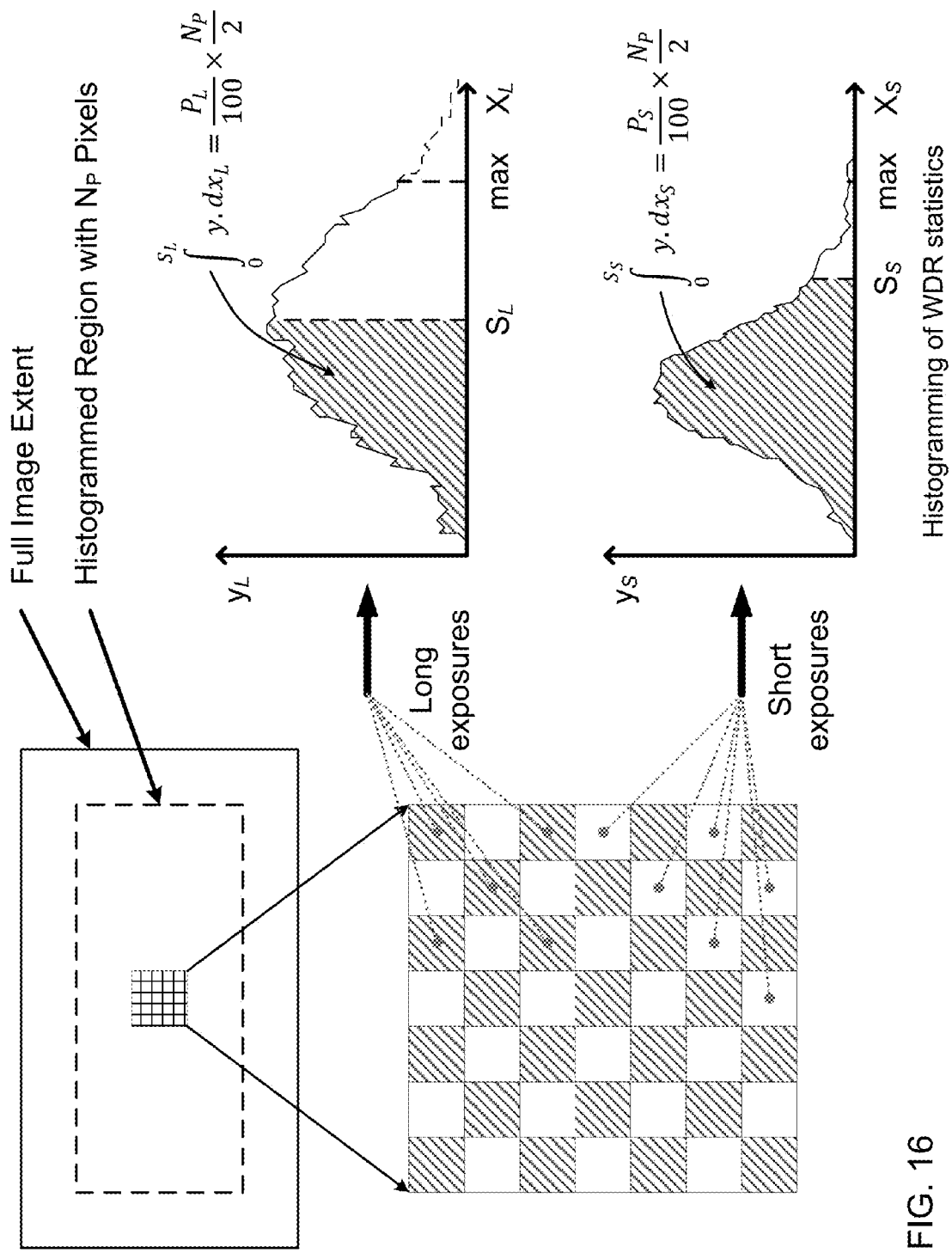
FIG. 16 illustrates a graphical representation of the operation of a pixel array having a plurality of exposure sensitivities over time in accordance with the principles and teachings of the disclosure.

For controlling the exposure time ratio (and thus the extent of the DR extension), WDR statistics may be gathered independently for the two flavors of pixel present in the checkerboard pattern. This may be optionally done independently for the red, green and blue frames too. Two corresponding histograms of black-corrected signal for a region of the image may be constructed. One of the histograms may be used, as mentioned earlier, to control the pulse energy level by comparing a chosen percentile ($P_L$) of the distribution to a target signal level ($S_L$, e.g. 50% of the digital DR). The exposure time of these type-1 pixels, $T_L$ may be held at maximum. The subscript L here denotes the long exposure. The other histogram may be used to monitor the DR of the scene by comparing another chosen percentile of the distribution, $P_S$, where $P_S>P_L$, and comparing that with a different signal level, $S_S$, where $S_S>S_L$. The subscript S denotes the short exposure. Ss may be generally tuned close to the top of the digital DR. If $P_S \leq S_S$, the exposure time for these type-2 pixels, $T_S$, may be also held at maximum. If $P_S>S_S$, then Ts may be lowered until $P_S=S_S$. See FIG. 16. There may be a predefined limit (E) as to how much the exposure time ratio may be allowed to increase, since at a certain point, the image quality degradation due to DR enhancement outweighs the benefit. The values of $P_L$, $P_S$, $S_L$, $S_S$ and E may be tuned differently according to different applications and stored as factory presets. The exposure times $T_L$ and $T_S$ may be recorded for each frame type, for use by the WDR fusion process (discussed further below) and by the color fusion ISP stage. In the case that the red, green and blue pulse energies may be modulated for the purpose of white balance, the exposure times on the red and blue frames may be governed by the green frames which may be exclusively used to gather the WDR statistics.

For the Y-Cb-Y-Cr illumination the three relative pulse energies may be held constant for a particular frame type. The WDR control may be applied for the luminance frames as a baseline with the option of also applying WDR independently on the chrominance frames. The histograms may be constructed on the raw black-corrected frame data as for the R-G-B-G scheme. Again the exposure times for each frame type may be recorded for WDR fusion and for color fusion.

Figure 17:
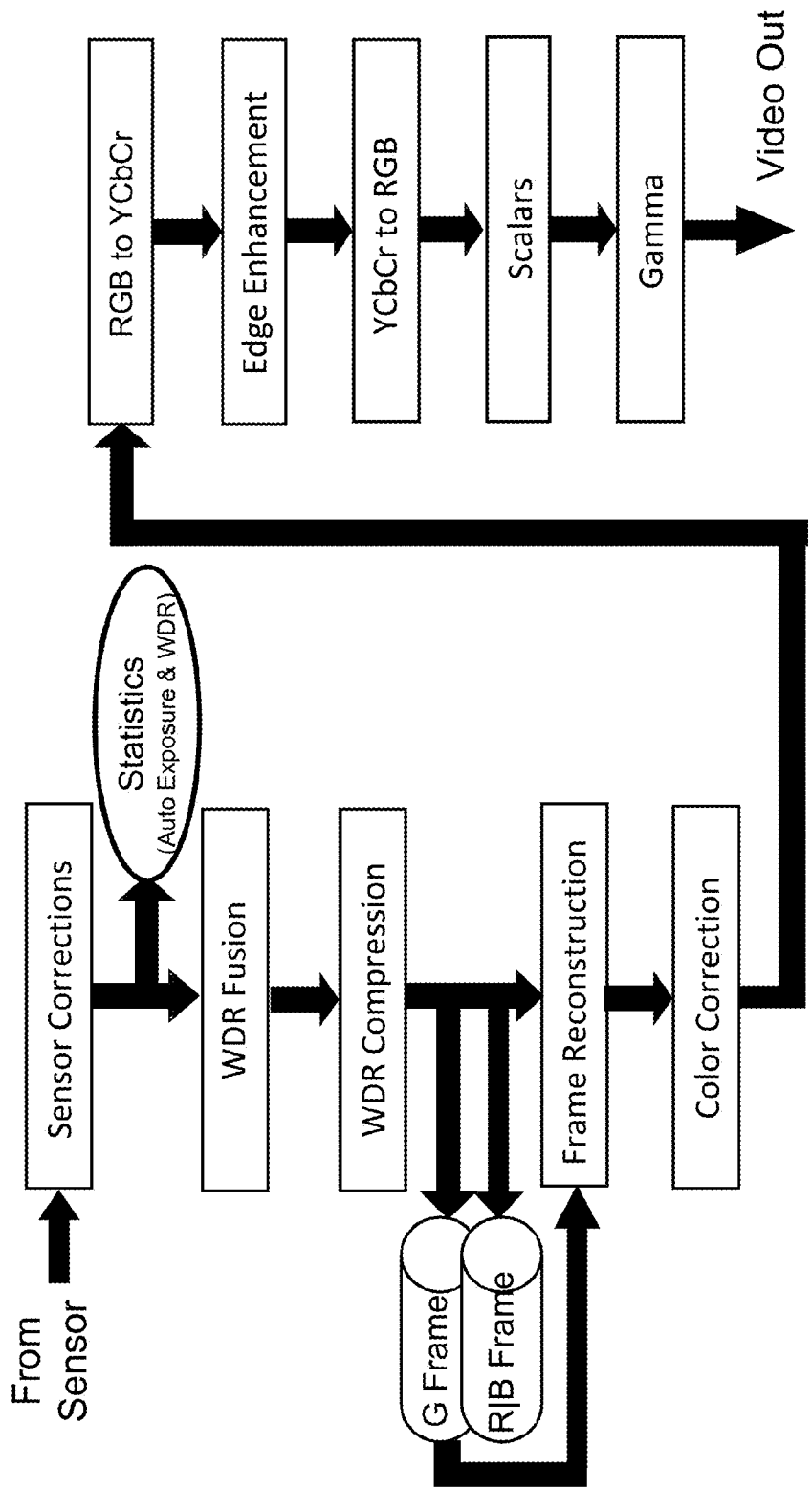
FIG. 17 illustrates a flow chart of an embodiment of an image sensor in accordance with the principles and teachings of the disclosure.

An embodiment may comprise wide dynamic range data being proceeded in the ISP. FIG. 17 shows the basic ISP arrangement for checkerboard WDR with the Y-Cb-Y-Cr pulsing scheme. It may be important that the WDR fusion comes after the dark frame subtraction so that the mean black offset has been adjusted to zero and the data may be signed. It may be also highly desirable to have had the FPN removed. The aim of the fusion process may be to combine for each frame, the data for the two separate exposures into single images, prior to color fusion. The first step involves separating the two components of the checkerboard pattern into two separate buffers and filling in the gaps by interpolation. There may be only one general kernel required since every empty pixel sees the same local environment, (except for pixels near the edges of the image). A suitable convolution kernel for filling in the checkerboard pattern by simple linear interpolation is:

$$\begin{pmatrix} 0 & \frac{1}{4} & 0 \\ \frac{1}{4} & 0 & \frac{1}{4} \\ 0 & \frac{1}{4} & 0 \end{pmatrix}$$

Figure 18:
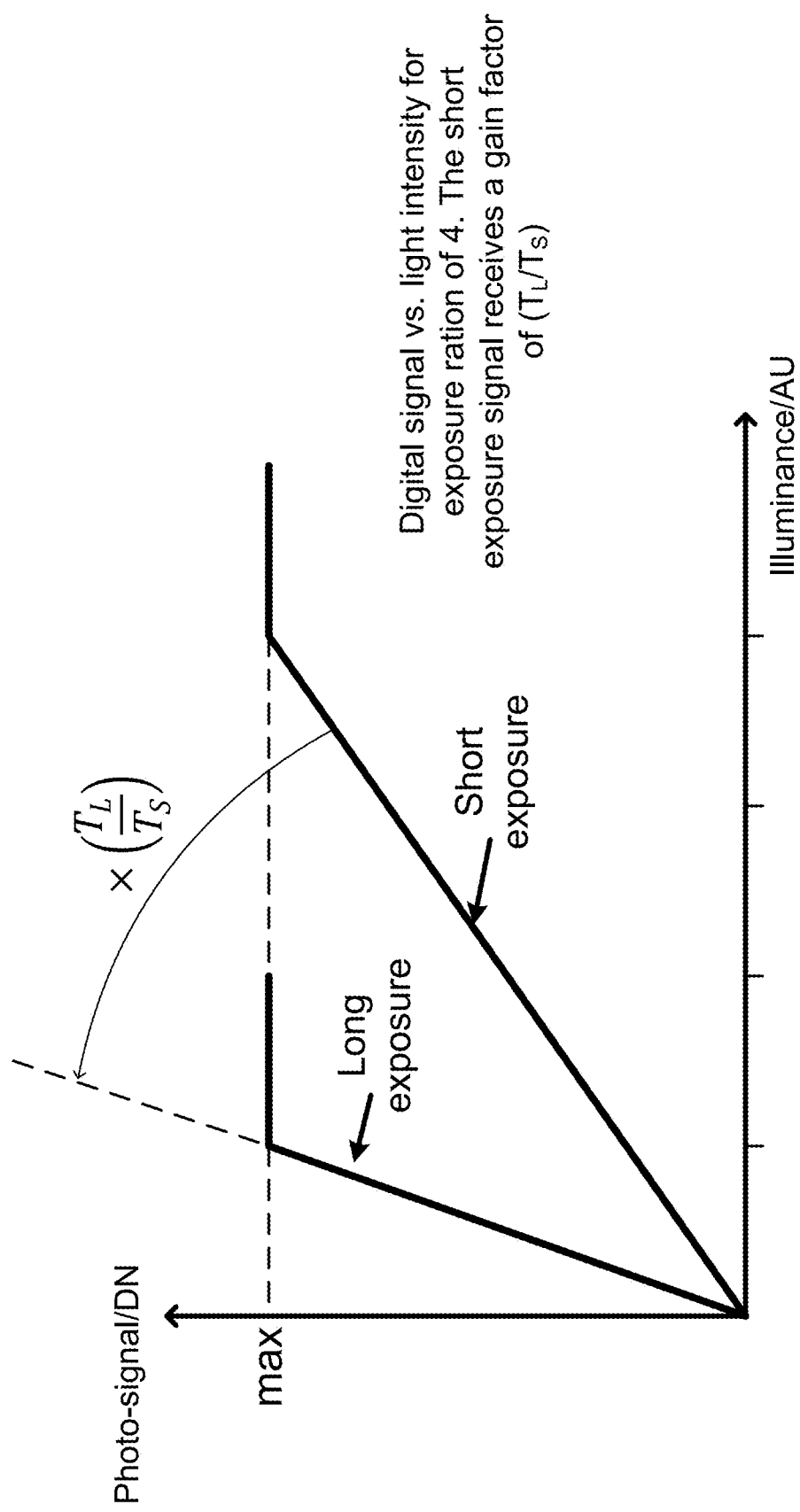
FIG. 18 illustrates a graphical representation of the exposure response of a sensor having a plurality of pixel sensitivities in accordance to the principles and teaching of the disclosure.
Figure 19:
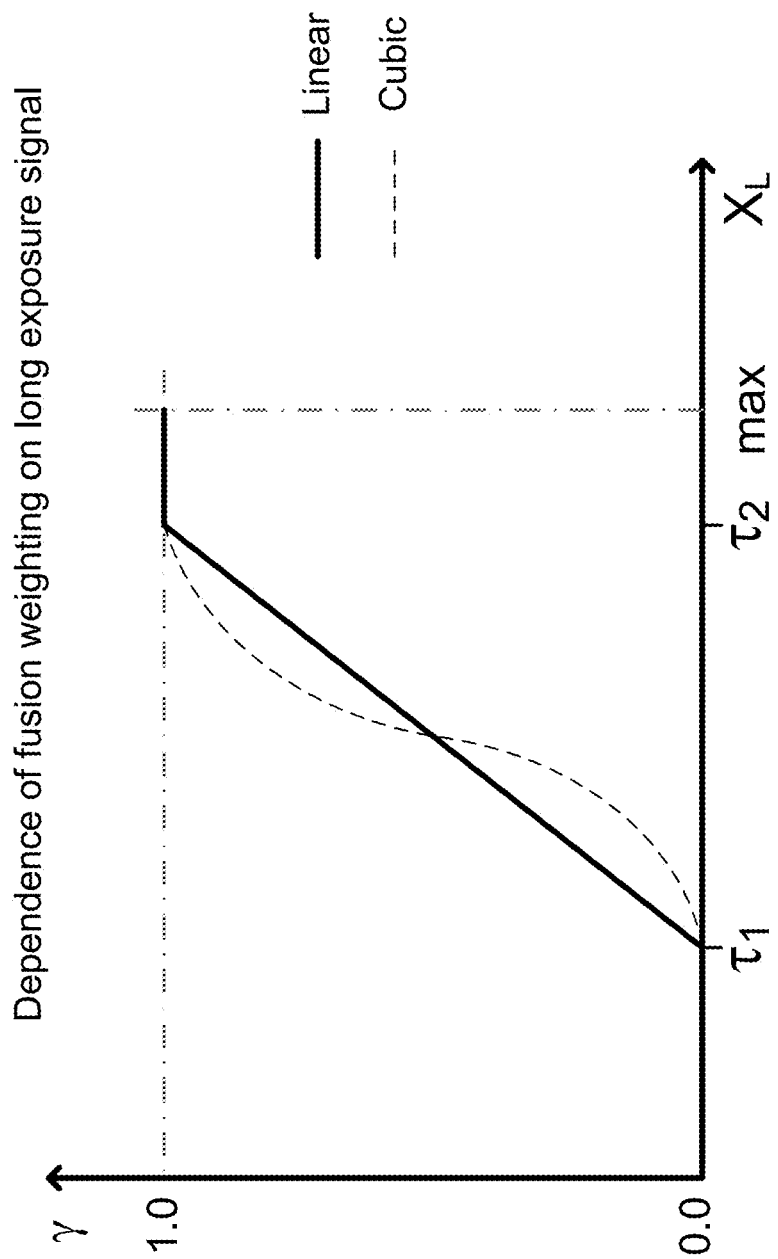
FIG. 19 illustrates a graphical representation of fusion weighting on a long exposure signal in accordance to the principles and teaching of the disclosure.

Following interpolation there may be two samples for each pixel location. FIG. 18 shows the illuminance—signal relations for an exposure ratio of 4 which would yield 12 dB of additional DR. A gain may be applied to the short exposure sample, which may be equal to the exposure-time ratio, $T_L/T_S$. This requires the addition of one extra bit for each factor 2 of ratio. The fusion itself involves making a weighted sum of the two samples:

$$x_f = \gamma \cdot \left(\frac{T_L}{T_S}\right) \cdot x_S + (1-\gamma)x_L$$

Where $x_S$ and $x_L$ may be the (signed) short and long exposure signals respectively. The γ factor may be a function of the long exposure signal, $x_L$, and may be set according to two thresholds, $\tau_1$ and $\tau_2$. Below $x_L=\tau_1$, γ=0.0, above γ=$\tau_2$, γ=1.0. Between the thresholds, various functional forms may be employed. See FIG. 19 in which linear and cubic example behaviors of γ between $\tau_1$ and $\tau_2$, may be drawn. The value of $\tau_2$ may be set to the maximum possible value of $x_L$, e.g., or something just below it. The purpose of the lower threshold, $\tau_1$, may be to limit the influence of read noise from the short sample which has the gain factor $T_L/T_S$ applied to it. It can be set to a conservatively high constant, to accommodate the maximum ratio E, but it may be more beneficial to have it vary linearly with $T_L/T_S$;

$$\tau_1 = \left(\frac{T_L}{T_S}\right) \cdot \eta$$

Figure 20:
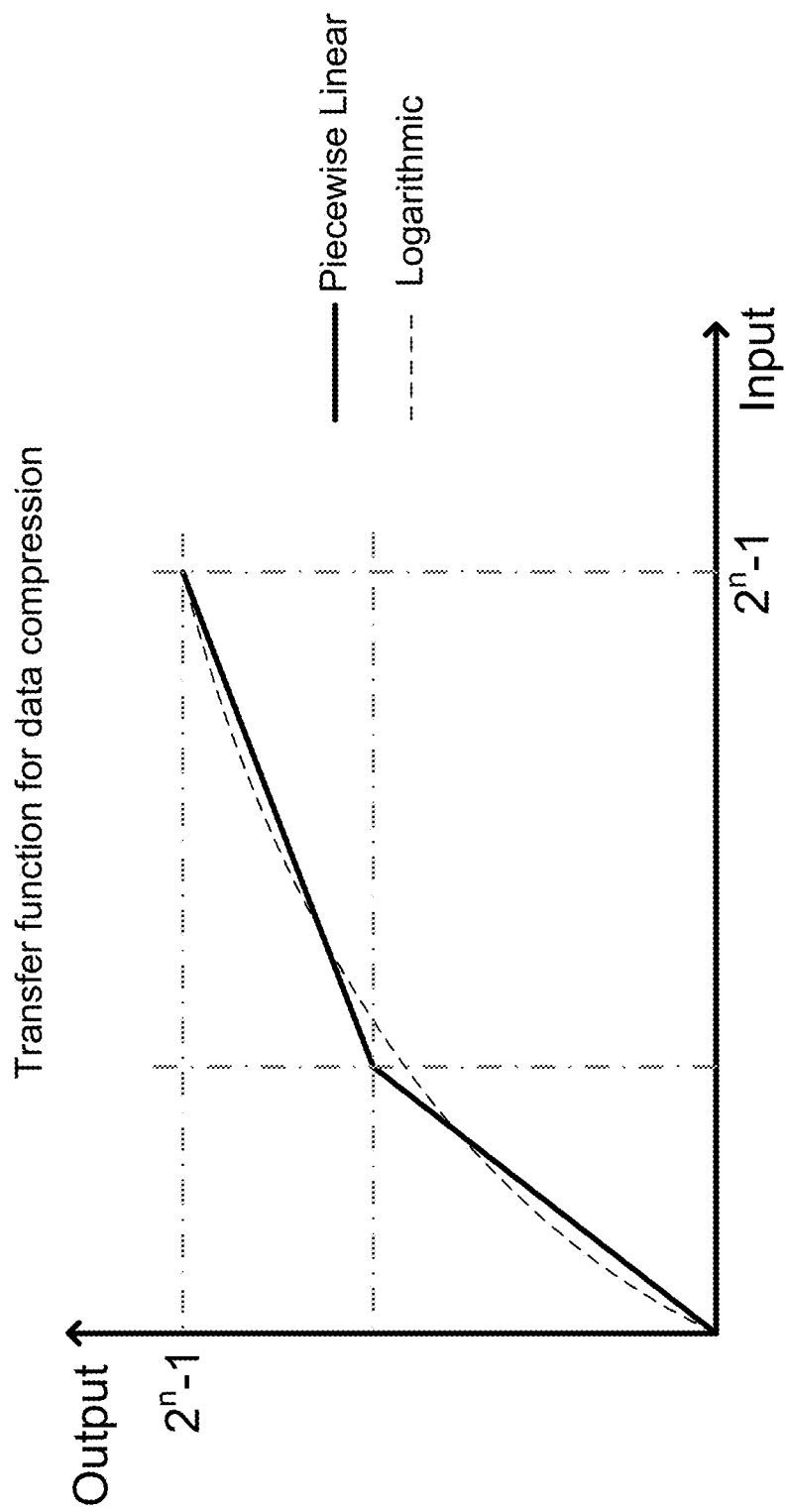
FIG. 20 illustrates a graphical representation of an embodiment of a transfer function for data compression in accordance to the principles and teaching of the disclosure.

Following the stitching process, the image data occupies a greater number of bits of digital dynamic range than the original long and short samples did, therefore it needs to have its bit count reduced back to the ISP pipeline width prior to the next stage. If ISP pipeline width may be n bits, the fused image has m bits where (m−n) may be the base-2 logarithm of the exposure time ratio, rounded up to the next integer. The data may be first linearly scaled such that the maximum possible value maps to exactly $2^m-1$. This can be accomplished e.g. by provision of a look-up table of multipliers, for the set of allowed exposure time ratios that lie between 1 and 2, to get to the next exact power of 2. This approach assumes the progression of allowed exposure time ratios within each power of 2-interval, may be always the same. To return to n bits, a piece-wise linear transfer function may be applied which emphasizes the data at the low end, see FIG. 20. This prevents interesting information at the low end being lost through compression. Alternatively, a smooth logarithmic transfer function can be applied to the data using a pre-defined look up table, similar to the gamma function. For this option the look up table needs to have sufficient entries to cover the maximum fused linear bit count ($m_{max}$). The fused data, already scaled to an exact power of 2 (i.e. in), would be further up-shifted to $m_{max}$ bits before applying the LUT.

Figure 21:
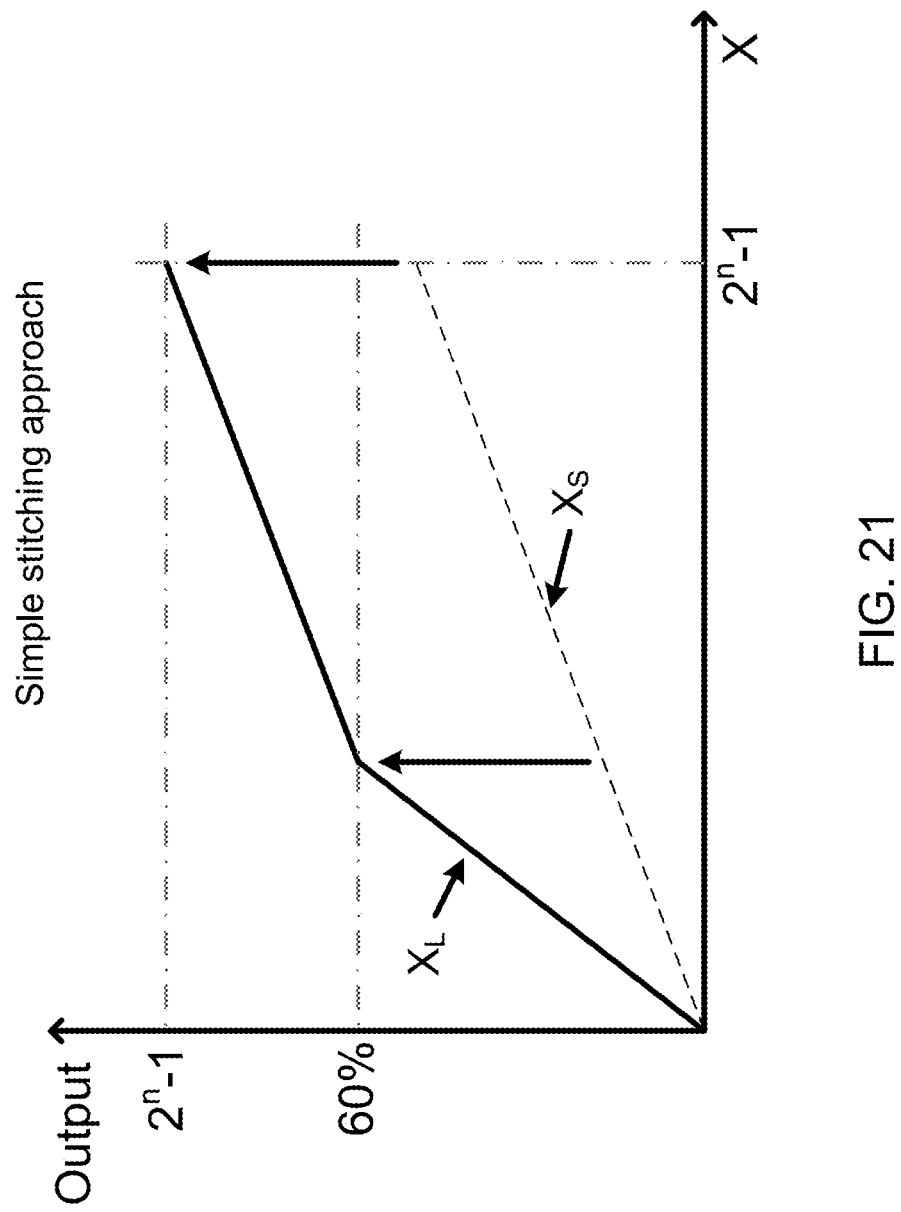
FIG. 21 illustrates a graphical representation of an embodiment for data compression in accordance to the principles and teaching of the disclosure.

A simpler, albeit less versatile overall approach to fusion and compression, may be to divide the final DR into 2 sections, for example the bottom 60% and the top 40%, and to map the long and short samples respectively, linearly into them. In the input domain, the crossover would e.g. occur at the maximum value of $x_L$. See FIG. 21.

The provision of 2 or more exposure periods within the same frame within a pulsed illumination endoscopy system may also be exploited for the purpose of reducing the number of captured frames per final full-color image, from three to two. This has an obvious benefit for suppressing possible color motion artifacts that may be associated with such a system.

Figure 22:
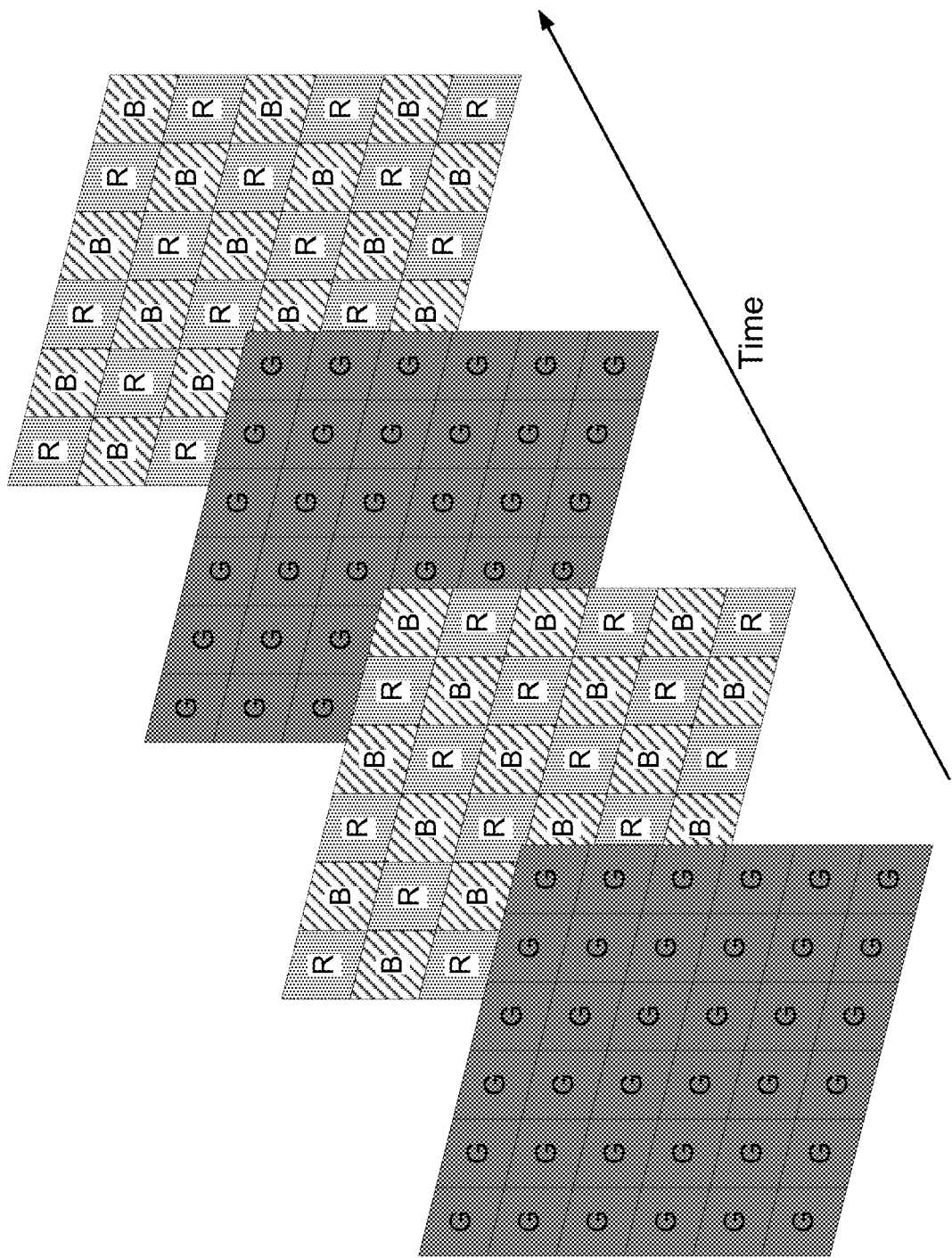
FIG. 22 illustrates an embodiment of a frame sequence pattern in accordance with the principles and teachings of the disclosure.
Figure 23:
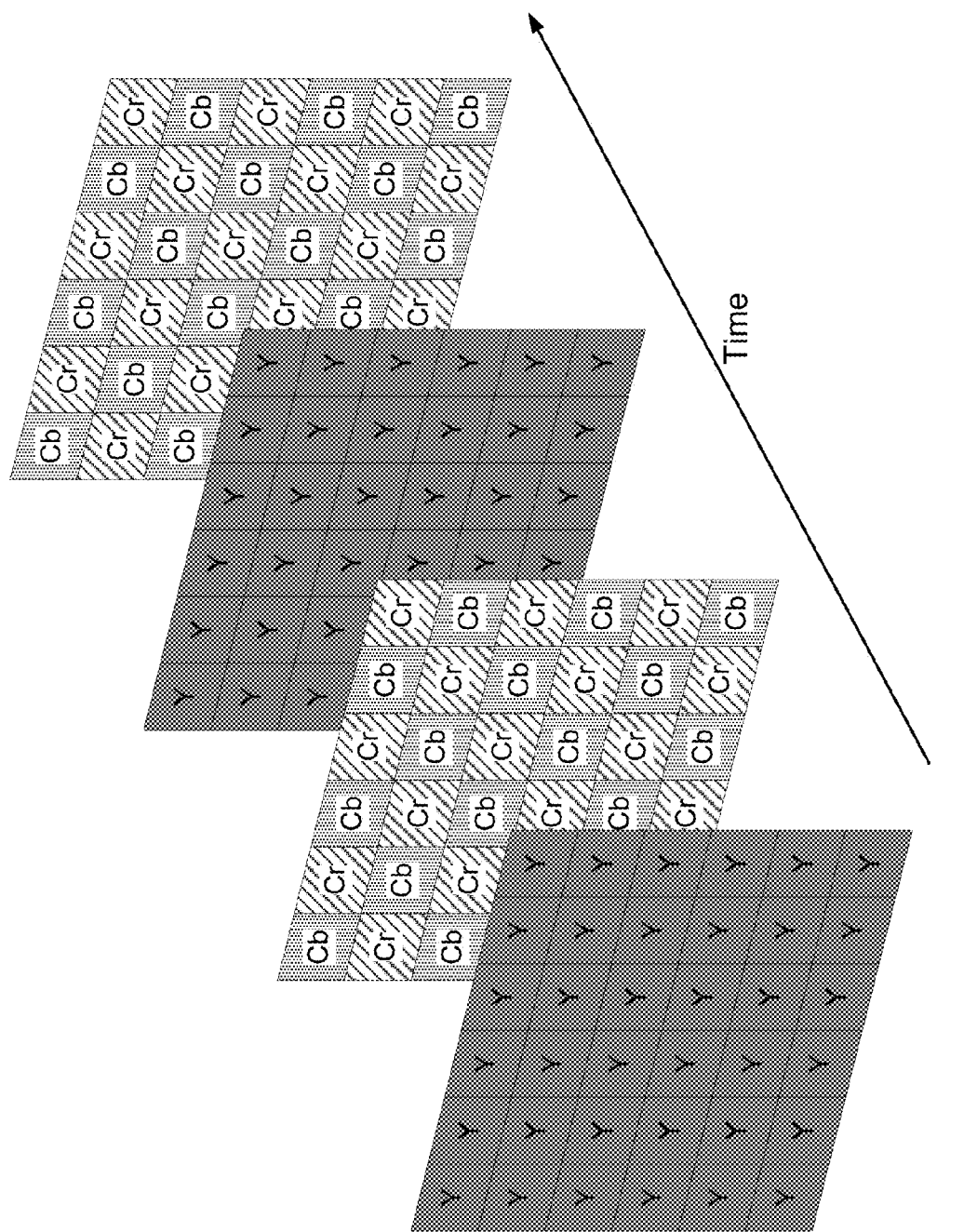
FIG. 23 illustrates an embodiment of a frame sequence pattern in accordance with the principles and teachings of the disclosure.

For the monochromatic pulsing approach, red and blue data may be combined in the same frame, while providing a full resolution frame of green pixels as shown in FIG. 22. This may be accomplished by virtue of changing the light content at the same time that the short exposure pixels start to integrate their signal. See FIG. 23. This limits the available dynamic range for chrominance, but DR may be not as important for color information as it may be for luminance since the cone receptors in the human retina may be far less sensitive than the rods. It also has the consequence of reducing the spatial resolution for chrominance but that also may be not an issue since the eye has greater resolution for luminance and chrominance may be usually spatially filtered within ISPs to reduce noise. In fact WDR can be exercised for the luminance frames at the same time that the exposure time duality may be used to combine the other two channels in a single frame.

An inherent property of the monochrome WDR array may be that the pixels that have the long integration time may be integrate a superset of the light seen by the short integration time pixels. For regular WiDy operation in the luminance frames, that may be desirable. For the chrominance frames it means that the pulsing may be controlled in conjunction with the exposure periods so as to e.g. provide λY+Cb from the start of the long exposure and switch to δY+Cr at the point that the short pixels may be turned on (both pixel types have their charges transferred at the same time). λ and δ may be two tunable factors that may be used to bring all pulse energies to positive values.

During color reconstruction in the ISP, the two flavors of pixel would be separated into two buffers. The empty pixels would be filled in using e.g. linear interpolation. At this point, one buffer would contain a full image of δY+Cr data and the other; δY+Cr+λY+Cb. The δY+Cr buffer would be subtracted from the second buffer to give λY+Cb. Then the appropriate proportion of luminance data from the Y frames would be subtracted out for each.

Figure 24:
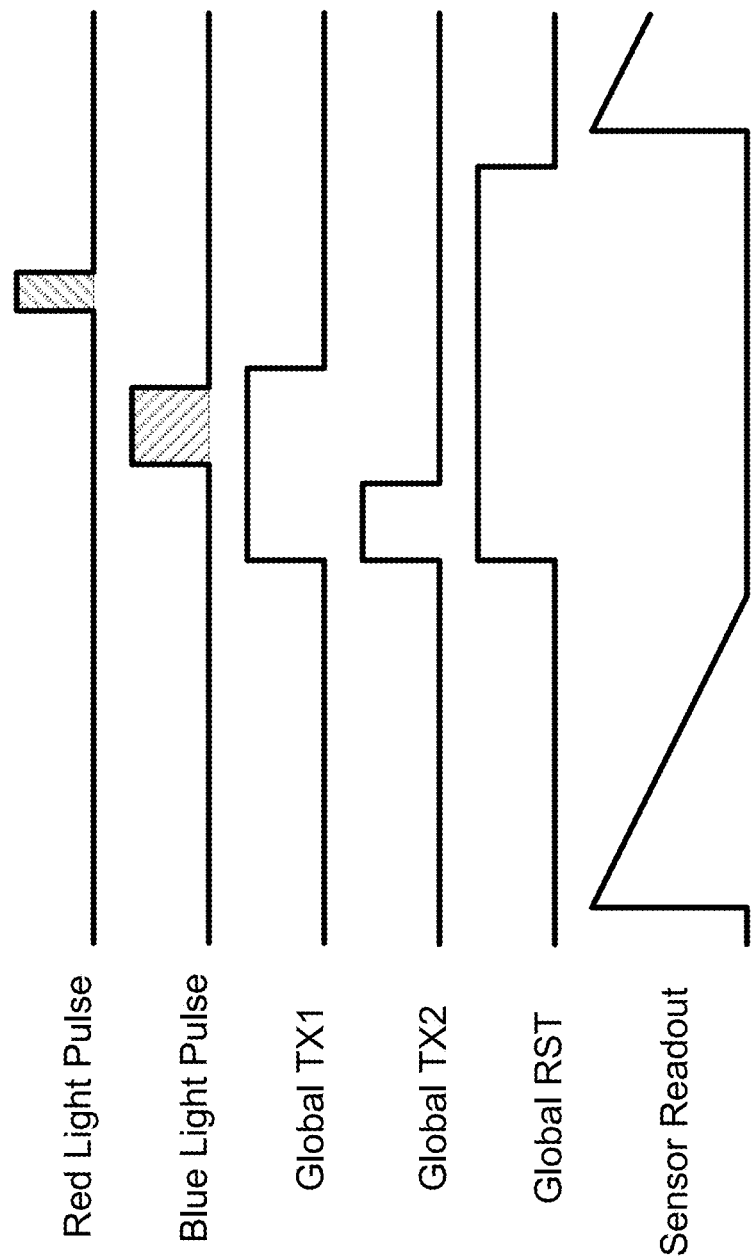
FIG. 24 illustrates an embodiment of a frame sequence pattern in accordance with the principles and teachings of the disclosure.

FIG. 24 depicts the timing of the light pulses with respect to the relevant sensor timing for the combined chrominance frame. Here, the proportion of mixed luminance may be critically tuned to reduce each chrominance situation to a single wavelength solution.

Implementations of the disclosure may comprise or utilize a special purpose or general-purpose computer including computer hardware, such as, for example, one or more processors and system memory, as discussed in greater detail below. Implementations within the scope of the disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions may be computer storage media (devices). Computer-readable media that carry computer-executable instructions may be transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" may be defined as one or more data links that enable the transport of electronic data between computer systems and/or modules and/or other electronic devices. In an implementation, a sensor and camera control unit may be networked in order to communicate with each other, and other components, connected over the network to which they may be connected. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures that can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. RAM can also include solid state drives (SSDs or PCIx based real time memory tiered Storage, such as FusionIO). Thus, it should be understood that computer storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts may be disclosed as example forms of implementing the claims.

Those skilled in the art will appreciate that the disclosure may be practiced in network computing environments with many types of computer system configurations, including, personal computers, desktop computers, laptop computers, message processors, control units, camera control units, hand-held devices, hand pieces, multi-processor systems, microprocessor-based or programmable consumer electronics, network PCs, minicomputers, mainframe computers, mobile telephones, PDAs, tablets, pagers, routers, switches, various storage devices, and the like. It should be noted that any of the above mentioned computing devices may be provided by or located within a brick and mortar location. The disclosure may also be practiced in distributed system environments where local and remote computer systems, which may be linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) or field programmable gate arrays can be programmed to carry out one or more of the systems and procedures described herein. Certain terms may be used throughout the following description and Claims to refer to particular system components. As one skilled in the art will appreciate, components may be referred to by different names. This document does not intend to distinguish between components that differ in name, but not function.

Figure 25:
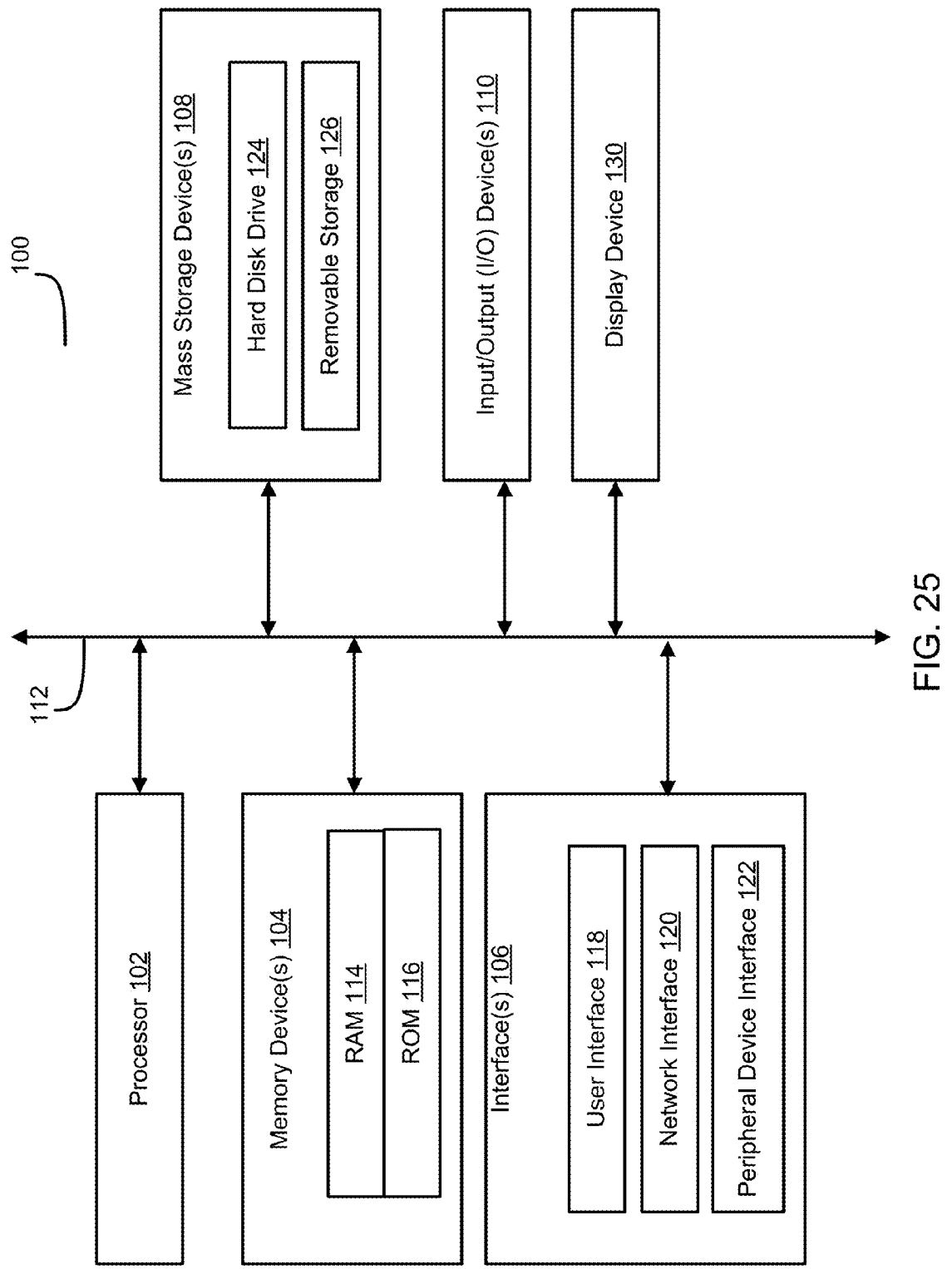
FIG. 25 illustrates an embodiment of hardware in accordance with the principles and teachings of the disclosure.

FIG. 25 is a block diagram illustrating an example computing device 100. Computing device 100 may be used to perform various procedures, such as those discussed herein. Computing device 100 can function as a server, a client, or any other computing entity. Computing device can perform various monitoring functions as discussed herein, and can execute one or more application programs, such as the application programs described herein. Computing device 100 can be any of a wide variety of computing devices, such as a desktop computer, a notebook computer, a server computer, a handheld computer, camera control unit, tablet computer and the like.

Computing device 100 includes one or more processor(s) 102, one or more memory device(s) 104, one or more interface(s) 106, one or more mass storage device(s) 108, one or more Input/Output (I/O) device(s) 110, and a display device 130 all of which may be coupled to a bus 112. Processor(s) 102 include one or more processors or controllers that execute instructions stored in memory device(s) 104 and/or mass storage device(s) 108. Processor(s) 102 may also include various types of computer-readable media, such as cache memory.

Memory device(s) 104 include various computer-readable media, such as volatile memory (e.g., random access memory (RAM) 114) and/or nonvolatile memory (e.g., read-only memory (ROM) 116). Memory device(s) 104 may also include rewritable ROM, such as Flash memory.

Mass storage device(s) 108 include various computer readable media, such as magnetic tapes, magnetic disks, optical disks, solid-state memory (e.g., Flash memory), and so forth. As shown in FIG. 25, a particular mass storage device is a hard disk drive 124. Various drives may also be included in mass storage device(s) 108 to enable reading from and/or writing to the various computer readable media. Mass storage device(s) 108 include removable media 126 and/or non-removable media.

I/O device(s) 110 include various devices that allow data and/or other information to be input to or retrieved from computing device 100. Example I/O device(s) 110 include digital imaging devices, electromagnetic sensors and emitters, cursor control devices, keyboards, keypads, microphones, monitors or other display devices, speakers, printers, network interface cards, modems, lenses, CCDs or other image capture devices, and the like.

Display device 130 includes any type of device capable of displaying information to one or more users of computing device 100. Examples of display device 130 include a monitor, display terminal, video projection device, and the like.

Interface(s) 106 include various interfaces that allow computing device 100 to interact with other systems, devices, or computing environments. Example interface(s) 106 may include any number of different network interfaces 120, such as interfaces to local area networks (LANs), wide area networks (WANs), wireless networks, and the Internet. Other interface(s) include user interface 118 and peripheral device interface 122. The interface(s) 106 may also include one or more user interface elements 118. The interface(s) 106 may also include one or more peripheral interfaces such as interfaces for printers, pointing devices (mice, track pad, etc.), keyboards, and the like.

Bus 112 allows processor(s) 102, memory device(s) 104, interface(s) 106, mass storage device(s) 108, and I/O device(s) 110 to communicate with one another, as well as other devices or components coupled to bus 112. Bus 112 represents one or more of several types of bus structures, such as a system bus, PCI bus, IEEE 1394 bus, USB bus, and so forth.

For purposes of illustration, programs and other executable program components may be shown herein as discrete blocks, although it is understood that such programs and components may reside at various times in different storage components of computing device 100, and may be executed by processor(s) 102. Alternatively, the systems and procedures described herein can be implemented in hardware, or a combination of hardware, software, and/or firmware. For example, one or more application specific integrated circuits (ASICs) can be programmed to carry out one or more of the systems and procedures described herein.

Figure 26A:
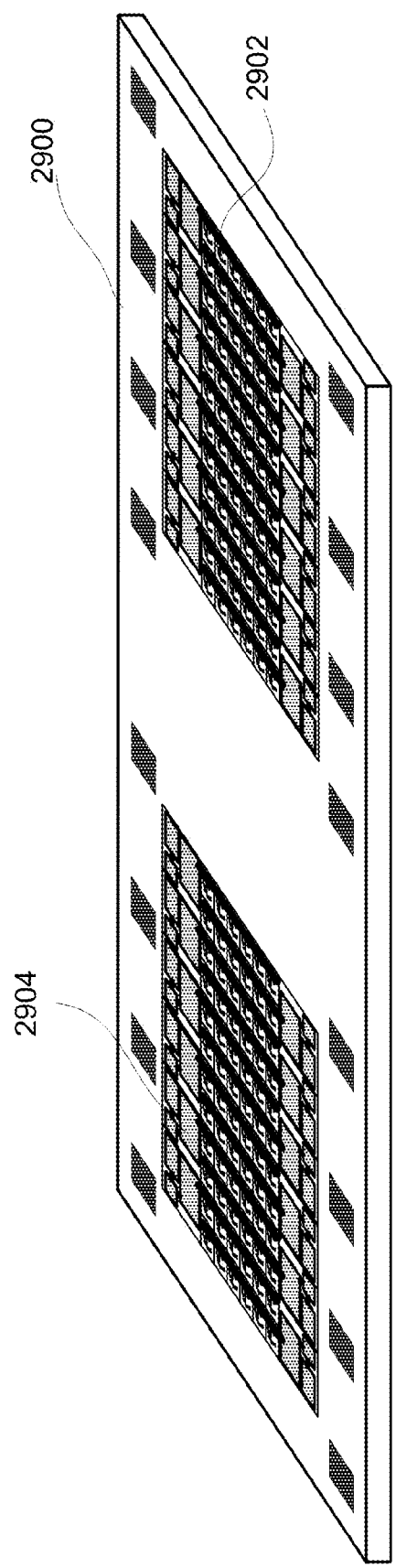
FIGS. 26A and 26B illustrate an implementation having a plurality of pixel arrays for producing a three dimensional image in accordance with the teachings and principles of the disclosure.
Figure 26B:
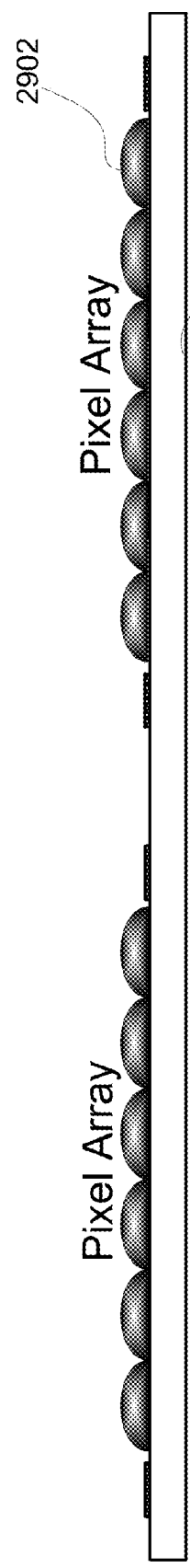

FIGS. 26A and 26B illustrate a perspective view and a side view, respectively, of an implementation of a monolithic sensor 2900 having a plurality of pixel arrays for producing a three dimensional image in accordance with the teachings and principles of the disclosure. Such an implementation may be desirable for three dimensional image capture, wherein the two pixel arrays 2902 and 2904 may be offset during use. In another implementation, a first pixel array 2902 and a second pixel array 2904 may be dedicated to receiving a predetermined range of wave lengths of electromagnetic radiation, wherein the first pixel array is dedicated to a different range of wave length electromagnetic radiation than the second pixel array.

Figure 27A:
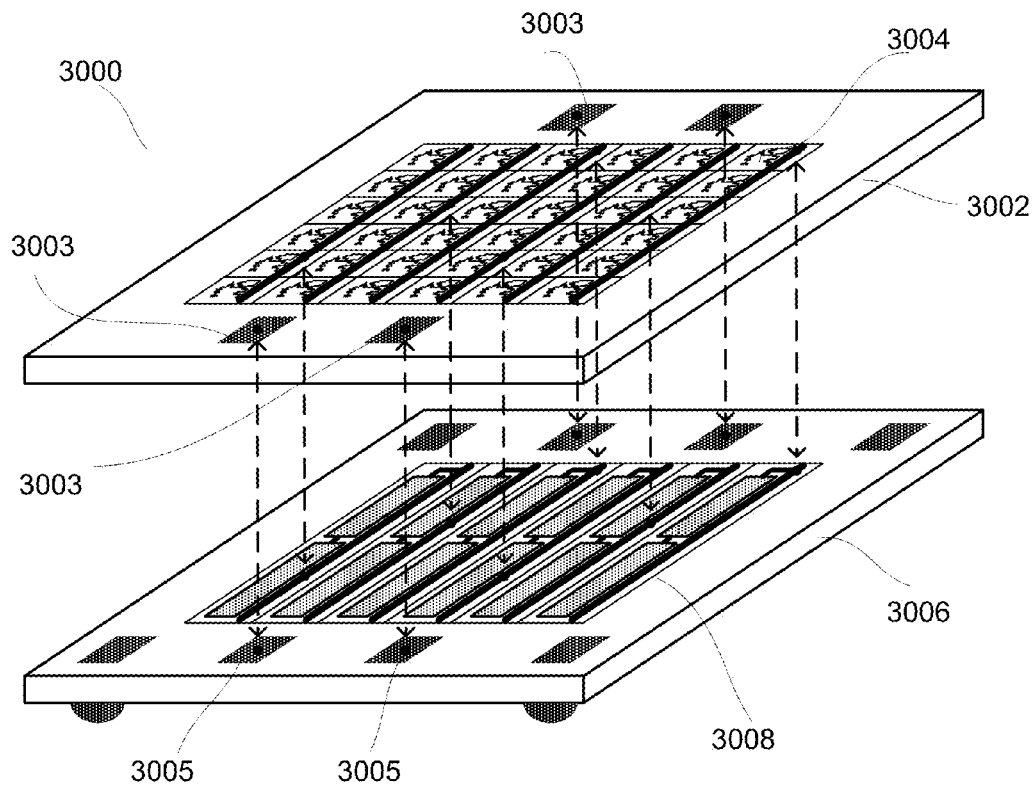
FIGS. 27A and 27B illustrate a perspective view and a side view, respectively, of an implementation of an imaging sensor built on a plurality of substrates, wherein a plurality of pixel columns forming the pixel array are located on the first substrate and a plurality of circuit columns are located on a second substrate and showing an electrical connection and communication between one column of pixels to its associated or corresponding column of circuitry.
Figure 27B:
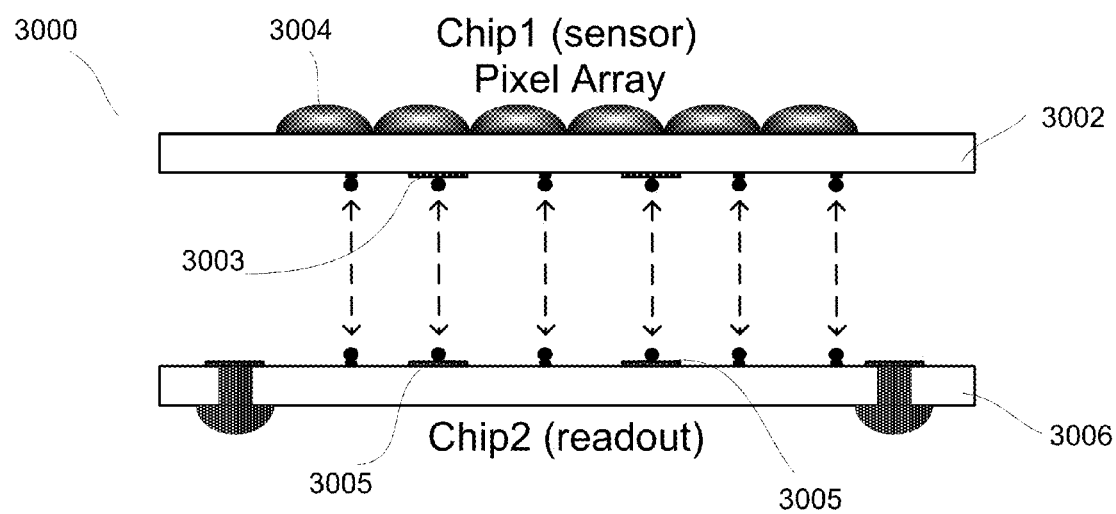

FIGS. 27A and 27B illustrate a perspective view and a side view, respectively, of an implementation of an imaging sensor 3000 built on a plurality of substrates. As illustrated, a plurality of pixel columns 3004 forming the pixel array are located on the first substrate 3002 and a plurality of circuit columns 3008 are located on a second substrate 3006. Also illustrated in the figure are the electrical connection and communication between one column of pixels to its associated or corresponding column of circuitry. In one implementation, an image sensor, which might otherwise be manufactured with its pixel array and supporting circuitry on a single, monolithic substrate/chip, may have the pixel array separated from all or a majority of the supporting circuitry. The disclosure may use at least two substrates/chips, which will be stacked together using three-dimensional stacking technology. The first 3002 of the two substrates/chips may be processed using an image CMOS process. The first substrate/chip 3002 may be comprised either of a pixel array exclusively or a pixel array surrounded by limited circuitry. The second or subsequent substrate/chip 3006 may be processed using any process, and does not have to be from an image CMOS process. The second substrate/chip 3006 may be, but is not limited to, a highly dense digital process in order to integrate a variety and number of functions in a very limited space or area on the substrate/chip, or a mixed-mode or analog process in order to integrate for example precise analog functions, or a RF process in order to implement wireless capability, or MEMS (Micro-Electro-Mechanical Systems) in order to integrate MEMS devices. The image CMOS substrate/chip 3002 may be stacked with the second or subsequent substrate/chip 3006 using any three-dimensional technique. The second substrate/chip 3006 may support most, or a majority, of the circuitry that would have otherwise been implemented in the first image CMOS chip 3002 (if implemented on a monolithic substrate/chip) as peripheral circuits and therefore have increased the overall system area while keeping the pixel array size constant and optimized to the fullest extent possible. The electrical connection between the two substrates/chips may be done through interconnects 3003 and 3005, which may be wirebonds, bump and/or TSV (Through Silicon Via).

FIGS. 28A and 28B illustrate a perspective view and a side view, respectively, of an implementation of an imaging sensor 3100 having a plurality of pixel arrays for producing a three dimensional image. The three dimensional image sensor may be built on a plurality of substrates and may comprise the plurality of pixel arrays and other associated circuitry, wherein a plurality of pixel columns 3104a forming the first pixel array and a plurality of pixel columns 3104b forming a second pixel array are located on respective substrates 3102a and 3102b, respectively, and a plurality of circuit columns 3108a and 3108b are located on a separate substrate 3106. Also illustrated are the electrical connections and communications between columns of pixels to associated or corresponding column of circuitry.

It will be appreciated that the teachings and principles of the disclosure may be used in a reusable device platform, a limited use device platform, a re-posable use device platform, or a single-use/disposable device platform without departing from the scope of the disclosure. It will be appreciated that in a re-usable device platform an end-user is responsible for cleaning and sterilization of the device. In a limited use device platform the device can be used for some specified amount of times before becoming inoperable. Typical new device is delivered sterile with additional uses requiring the end-user to clean and sterilize before additional uses. In a re-posable use device platform a third-party may reprocess the device (e.g., cleans, packages and sterilizes) a single-use device for additional uses at a lower cost than a new unit. In a single-use/disposable device platform a device is provided sterile to the operating room and used only once before being disposed of.

Additionally, the teachings and principles of the disclosure may include any and all wavelengths of electromagnetic energy, including the visible and non-visible spectrums, such as infrared (IR), ultraviolet (UV), and X-ray.

It will be appreciated that various features disclosed herein provide significant advantages and advancements in the art. The following embodiments may be exemplary of some of those features.

In the foregoing Detailed Description of the Disclosure, various features of the disclosure may be grouped together in a single embodiment for the purpose of streamlining the disclosure. This method of disclosure is not to be interpreted as reflecting an intention that the claimed disclosure requires more features than may be expressly recited in each claim. Rather, inventive aspects lie in less than all features of a single foregoing disclosed embodiment.

It is to be understood that the above-described arrangements may be only illustrative of the application of the principles of the disclosure. Numerous modifications and alternative arrangements may be devised by those skilled in the art without departing from the spirit and scope of the disclosure and the appended claims may be intended to cover such modifications and arrangements.

Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms may be used throughout the following description and Claims to refer to particular system components. As one skilled in the art will appreciate, components may be referred to by different names. This document does not intend to distinguish between components that differ in name, but not function.

The foregoing description has been presented for the purposes of illustration and description. It is not intended to be exhaustive or to limit the disclosure to the precise form disclosed. Many modifications and variations may be possible in light of the above teaching. Further, it should be noted that any or all of the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A method for imaging in a light deficient environment comprising:
    emitting four electromagnetic radiation pulses of three different wavelengths into a light deficient environment during a blanking period during frame capture of an image sensor, wherein the image sensor comprises a plurality of pixels, and wherein the image sensor comprises a monochromatic image sensor;
    capturing a plurality of frames in the light deficient environment using the image sensor, each one of the plurality of frames being radiated by one of the four electromagnetic radiation pulses of the three different wavelengths, wherein capturing at least one frame of the plurality frames comprises controlling a first subset of pixels during the at least one frame for a long exposure and controlling a second subset of pixels during the at least one frame for a short exposure, wherein the at least one frame for the long exposure and the at least one frame for the short exposure are two of the plurality of frames that are exposed to the same wavelength of electromagnetic radiation; and
    creating a single display frame from the plurality of frames.

2. The method of claim 1, further comprising:
    creating a stream of display frames by repeating the emitting electromagnetic radiation into the light deficient environment, the capturing the plurality of frames, and the creating the single display frame from the plurality of frames; and
    providing the stream of display frames as a video stream.

3. The method of claim 1, wherein each of the pixels comprises a transfer gate transistor (TX).

4. The method of claim 3, wherein each TX in a subgroup of pixels is electrically connected together by a common TX line.

5. The method of claim 3, wherein the TX line provides global operation of transfer gate transistors for the subgroup of pixels.

6. The method of claim 1, wherein two or more pixels of the image sensor share a floating diffusion in a pixel share, wherein a first subgroup of pixels in the first subset is connected by a first TX line and a second subgroup of pixels in the second subset is connected by a second TX line.

7. The method of claim 6, wherein the two or more pixels are within a same row of pixels of the image sensor.

8. The method of claim 6, wherein global operation of the first TX line and the second TX line is performed during the blanking period.

9. The method of claim 6, wherein controlling the first subset of pixels during the at least one frame for the long exposure and controlling the second subset of pixels during the at least one frame for the short exposure comprises actuating the first TX line at a different time than the second TX line.

10. The method of claim 1, wherein the first subset of pixels and the second subset of pixels are arranged in a checkerboard pattern.

11. The method of claim 1, further comprising capturing at least a second frame during which the first subset of pixels is exposed for the short exposure and the second subset of pixels are exposed for the long exposure, wherein the long exposure comprises a longer length of time than the short exposure.

12. The method of claim 1, wherein emitting the electromagnetic radiation into the light deficient environment comprises controlling the emitter to pulse electromagnetic energy at a plurality of exposures corresponding to subsets of different pixels of the image sensor.

13. A system for digital imaging in a light deficient environment:
    an emitter for providing illumination using electromagnetic pulses of a plurality of different wavelengths;
    a monochromatic image sensor comprising a plurality of pixels that are sensitive to the electromagnetic pulses; and
    a controller that causes the system to:
        emit four electromagnetic radiation pulses of three different wavelengths into a light deficient environment during a blanking period during frame capture of the image sensor;
        capture a plurality of frames in the light deficient environment using the image sensor, each one of the plurality of frames being radiated by one of the four electromagnetic pulses of the three different wavelengths, wherein capturing at least one frame of the repeating frames comprises controlling a first subset of pixels during the at least one frame for a long exposure and controlling a second subset of pixels during the at least one frame for a short exposure, wherein the at least one frame for the long exposure and the at least one frame for the short exposure are two of the plurality of frames that are exposed to the same wavelength of electromagnetic radiation; and
        create a single display frame from the plurality of frames.

14. The system of claim 13, wherein the controller causes the system to:
    create a stream of display frames by repeating the emitting electromagnetic radiation into the light deficient environment, the capturing the plurality of frames, and the creating the single display frame from the plurality of frames; and
    provide the stream of display frames as a video stream.

15. The system of claim 13, wherein each of the pixels of the image sensor comprises a transfer gate transistor (TX).

16. The system of claim 15, wherein each TX in a subgroup of pixels is electrically connected together by a common TX line.

17. The system of claim 15, wherein the TX line provides global operation of transfer gate transistors for the subgroup of pixels.

18. The system of claim 13, wherein two or more pixels of the image sensor share a floating diffusion in a pixel share, wherein a first subgroup of pixels in the first subset is connected by a first TX line and a second subgroup of pixels in the second subset is connected by a second TX line.

19. The system of claim 18, wherein the two or more pixels are within a same row of pixels of the image sensor.

20. The system of claim 18, wherein global operation of the first TX line and the second TX line is performed during the blanking period.

21. The system of claim 18, wherein the controller controls the first subset of pixels during the at least one frame for the long exposure and controls the second subset of pixels during the at least one frame for the short exposure by actuating the first TX line at a different time than the second TX line.

22. The system of claim 13, wherein the first subset of pixels and the second subset of pixels are arranged in a checkerboard pattern in the image sensor.

23. The system of claim 13, wherein the controller further controls the system to capture at least a second frame during which the first subset of pixels is exposed for the short exposure and the second subset of pixels are exposed for the long exposure, wherein the long exposure comprises a longer length of time than the short exposure.

24. The system of claim 13, wherein the controller causes the system to emit the electromagnetic radiation into the light deficient environment by controlling the emitter to pulse electromagnetic energy at a plurality of exposures corresponding to subsets of different pixels of the image sensor.

25. Non-transitory computer readable storage media storing instructions that, when executed by one or more processors, cause the one or more processors to:
   emit four electromagnetic radiation pulses of three different wavelengths into a light deficient environment during a blanking period during frame capture of an image sensor, wherein the image sensor comprises a plurality of pixels, and wherein the image sensor comprises a monochromatic image sensor;
   capture a plurality of frames in the light deficient environment using the image sensor, each one of the plurality of frames being radiated by one of the four electromagnetic radiation pulses of the three different wavelengths, wherein capturing at least one frame of the repeating frames comprises controlling a first subset of pixels during the at least one frame for a long exposure and controlling a second subset of pixels during the at least one frame for a short exposure, wherein the at least one frame for the long exposure and the at least one frame for the short exposure are two of the plurality of frames that are exposed to the same wavelength of electromagnetic radiation; and
   create a single display frame from the plurality of frames.

26. The computer readable storage media of claim 25, wherein the instructions further cause the one or more processors to:
   create a stream of display frames by repeating the emitting electromagnetic radiation into the light deficient environment, the capturing the plurality of frames, and the creating the single display frame from the plurality of frames; and
   provide the stream of display frames as a video stream.

27. The computer readable storage media of claim 25, wherein each of the pixels of the image sensor comprises a transfer gate transistor (TX).

28. The computer readable storage media of claim 27, wherein each TX in a subgroup of pixels is electrically connected together by a common TX line.

29. The computer readable storage media of claim 27, wherein the TX line provides global operation of transfer gate transistors for the subset of pixels.

30. The computer readable storage media of claim 25, wherein two or more pixels of the image sensor share a floating diffusion in a pixel share, wherein a first subgroup of pixels in the first subset is connected by a first TX line and a second subgroup of pixels in the second subset is connected by a second TX line.

31. The computer readable storage media of claim 30, wherein the two or more pixels are within a same row of pixels of the image sensor.

32. The computer readable storage media of claim 30, wherein the instructions cause global operation of the first TX line and the second TX line to be performed during the blanking period.

33. The computer readable storage media of claim 30, wherein the instructions cause the one or more processors to control the first subset of pixels during the at least one frame for the long exposure and control the second subset of pixels during the at least one frame for the short exposure by actuating the first TX line at a different time than the second TX line.

34. The computer readable storage media of claim 25, wherein the first subset of pixels and the second subset of pixels are arranged in a checkerboard pattern in the image sensor.

35. The computer readable storage media of claim 25, wherein the instructions further cause the one or more processors to capture at least a second frame during which the first subset of pixels is exposed for the short exposure and the second subset of pixels are exposed for the long exposure, wherein the long exposure comprises a longer length of time than the short exposure.

36. The computer readable storage media of claim 25, wherein the instructions further cause the one or more processors to emit the electromagnetic radiation into the light deficient environment by controlling the emitter to pulse electromagnetic energy at a plurality of exposures corresponding to subsets of different pixels of the image sensor.

* * * * *